(12) United States Patent
Tomimatsu et al.

(10) Patent No.: US 10,350,214 B2
(45) Date of Patent: Jul. 16, 2019

(54) PREPARATION CONTAINING TETRACYCLIC COMPOUND AT HIGH DOSE

(71) Applicant: Chugai Seiyaku Kabushiki Kaisha, Kita-ku, Tokyo (JP)

(72) Inventors: Takashi Tomimatsu, Tokyo (JP); Kensuke Okazaki, Tokyo (JP); Yumi Ogawa, Tokyo (JP); Takahiro Yamamura, Tokyo (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/304,133

(22) PCT Filed: Apr. 24, 2015

(86) PCT No.: PCT/JP2015/062520
§ 371 (c)(1),
(2) Date: Oct. 14, 2016

(87) PCT Pub. No.: WO2015/163448
PCT Pub. Date: Oct. 29, 2015

(65) Prior Publication Data
US 2017/0035773 A1 Feb. 9, 2017

(30) Foreign Application Priority Data
Apr. 25, 2014 (JP) .................. 2014-092101

(51) Int. Cl.
*A61K 31/5377* (2006.01)
*A61K 47/20* (2006.01)
(Continued)

(52) U.S. Cl.
CPC ............ *A61K 31/5377* (2013.01); *A61K 9/16* (2013.01); *A61K 9/1617* (2013.01);
(Continued)

(58) Field of Classification Search
CPC .... A61K 31/5377; A61K 47/20; A61K 47/36; A61K 47/38; A61K 9/16; A61K 9/48; A61K 9/1617; C07D 401/04
See application file for complete search history.

(56) References Cited

U.S. PATENT DOCUMENTS 5,028,433 A    7/1991  Ishimaru et al.
5,721,267 A    2/1998  Broka
(Continued)

FOREIGN PATENT DOCUMENTS

CN        1902200 A    1/2007
EA        001450 B1    4/2001
(Continued)

OTHER PUBLICATIONS

Kinoshita et al. "Design and synthesis of a highly selective, orally active and potent anaplastic lymphoma kinase inhibitor (CH5424802)" in Bioorganic and Medicinal Chemistry, 20 (2012) 1271-1280.*
(Continued)

*Primary Examiner* — Blessing M Fubara
(74) *Attorney, Agent, or Firm* — Foley & Lardner LLP

(57) ABSTRACT

An improved solubility of a pharmaceutical composition or formulation containing a large amount of 9-ethyl-6,6-dimethyl-8-(4-morpholin-4-yl-piperidin-1-yl)-11-oxo-6,11-dihydro-5H-benzo[b]carbazole-3-carbonitrile or a salt thereof can be achieved by forming granules of the compound or salt thereof and allowing the granules to be present together with a disintegrating agent.

24 Claims, 6 Drawing Sheets

(51) Int. Cl.
    *A61K 47/36*     (2006.01)
    *A61K 47/38*     (2006.01)
    *A61K 9/16*     (2006.01)
    *A61K 9/48*     (2006.01)
    *C07D 401/04*     (2006.01)

(52) U.S. Cl.
    CPC .............. *A61K 9/1652* (2013.01); *A61K 9/48* (2013.01); *A61K 47/20* (2013.01); *A61K 47/36* (2013.01); *A61K 47/38* (2013.01); *C07D 401/04* (2013.01)

(56) References Cited

U.S. PATENT DOCUMENTS

| | | | |
|---|---|---|---|
| 5,936,084 | A | 8/1999 | Jirousek et al. |
| 7,125,565 | B2 | 10/2006 | Sugishita et al. |
| 7,799,860 | B2 | 9/2010 | Sugishita |
| 9,126,931 | B2 | 9/2015 | Kinoshita et al. |
| 9,365,514 | B2 | 6/2016 | Furumoto et al. |
| 9,440,922 | B2 | 9/2016 | Kinoshita et al. |
| 2004/0076675 | A1 | 4/2004 | Sugishita et al. |
| 2004/0156902 | A1 | 8/2004 | Lee et al. |
| 2005/0107364 | A1 | 5/2005 | Hutchinson et al. |
| 2007/0031907 | A1 | 2/2007 | Pinna et al. |
| 2007/0060595 | A1 | 3/2007 | Yoshizawa et al. |
| 2007/0065516 | A1 | 3/2007 | Sugishita et al. |
| 2007/0099893 | A1 | 5/2007 | Boyd et al. |
| 2007/0249653 | A1 | 10/2007 | Jagtap et al. |
| 2008/0058320 | A1 | 3/2008 | Herold et al. |
| 2008/0085309 | A1* | 4/2008 | Tsushima ............. A61K 9/0056 424/464 |
| 2008/0090776 | A1 | 4/2008 | Mano et al. |
| 2008/0262021 | A1 | 10/2008 | Capraro et al. |
| 2009/0099193 | A1 | 4/2009 | Mano et al. |
| 2009/0214648 | A1* | 8/2009 | Kandakatla .......... A61K 9/2054 424/482 |
| 2009/0221555 | A1 | 9/2009 | Ahmed et al. |
| 2010/0099658 | A1 | 4/2010 | Kondoh et al. |
| 2010/0240673 | A1 | 9/2010 | Mano et al. |
| 2011/0230545 | A1 | 9/2011 | Mano et al. |
| 2012/0083488 | A1 | 4/2012 | Kinoshita et al. |
| 2013/0143877 | A1* | 6/2013 | Furumoto ............ A61K 9/1641 514/232.8 |
| 2013/0203723 | A1 | 8/2013 | Sakuma et al. |
| 2015/0071919 | A1* | 3/2015 | White .................... A61K 33/24 424/133.1 |
| 2015/0272958 | A1 | 10/2015 | Kodama et al. |
| 2016/0317494 | A1 | 11/2016 | Furumoto et al. |
| 2016/0340308 | A1 | 11/2016 | Kinoshita et al. |
| 2017/0035773 | A1 | 2/2017 | Tomimatsu et al. |
| 2017/0081306 | A1 | 3/2017 | Tanaka et al. |
| 2017/0119781 | A1 | 5/2017 | Meier et al. |

FOREIGN PATENT DOCUMENTS

| | | |
|---|---|---|
| EP | 1364643 A1 | 11/2003 |
| EP | 1914240 B1 | 12/2009 |
| JP | 02-223522 A | 9/1990 |
| JP | 08-092090 A | 4/1996 |
| JP | 09-202728 A | 8/1997 |
| JP | 2008-280352 A | 11/2008 |
| JP | 2009-100783 A | 5/2009 |
| JP | 4588121 B1 | 9/2010 |
| JP | 4918630 B1 | 2/2012 |
| JP | 2012-126711 A | 7/2012 |
| RU | 2162089 C2 | 1/2001 |
| RU | 2387650 C2 | 4/2010 |
| WO | WO 00/69856 A1 | 11/2000 |
| WO | WO 02/043704 A1 | 6/2002 |
| WO | WO 2004/080980 A1 | 9/2004 |
| WO | WO 2005/009389 A2 | 2/2005 |
| WO | WO 2005/097765 A1 | 10/2005 |
| WO | WO 2006/021884 A2 | 3/2006 |
| WO | WO 2007/023310 A2 | 3/2007 |
| WO | WO 2007/056497 A1 | 5/2007 |
| WO | WO 2007/066185 A2 | 6/2007 |
| WO | WO 2007/130468 A2 | 11/2007 |
| WO | WO 2008/021369 A2 | 2/2008 |
| WO | WO 2008/051547 A1 | 5/2008 |
| WO | WO 2008/130951 A1 | 10/2008 |
| WO | WO 2009/008371 A1 | 1/2009 |
| WO | WO 2009/013126 A1 | 1/2009 |
| WO | WO 2009/073620 A2 | 6/2009 |
| WO | WO 2010/128324 A1 | 11/2010 |
| WO | WO 2010/142423 A2 | 12/2010 |
| WO | WO 2010/142685 A1 | 12/2010 |
| WO | WO 2010/143664 A1 | 12/2010 |
| WO | WO 2012023597 A1 * | 2/2012 |
| WO | WO 2012/043709 A1 | 4/2012 |

OTHER PUBLICATIONS

Sakamoto et al. "CH5424802, a selective ALK inhibitor capable of blocking the resistant gatekeeper mutant" in Cancer Cell, May 17, 2011;19(5):679-690. doi: 10.1016/j.ccr.2011.04.004.*
Bunz, F., "Chapter 1, The Genetic Basis of Cancer," Principles of Cancer Genetics, 2008, 1-47.
CAS RN 100863-39-6, STN Entry Date Mar. 15, 1986.
CAS RN 222318-66-3, STN Entry Date May 7, 1999.
CAS RN 24716-14-1, STN Entry Date Nov. 16, 1984.
CAS RN 36263-63-5, STN Entry Date Nov. 16, 1984.
CAS RN 4355-38-8, STN Entry Date Nov. 16, 1984.
CAS RN 6008-29-3, STN Entry Date Nov. 16, 1984.
CAS RN 61492-49-7, STN Entry Date Nov. 16, 1984.
CAS RN 74205-47-3, STN Entry Date Nov. 16, 1984.
CAS RN 89579-57-7, STN Entry Date Nov. 16, 1984.
CAS RN 93257-39-7, STN Entry Date Dec. 18, 1984.
Chen et al., "Oncogenic mutations of ALK kinase in neuroblastoma," Nature, Oct. 16, 2008, 455:971-974, and Methods page.
Cools et al., "Identification of Novel Fusion Partners of ALK, the Anaplastic Lymphoma Kinase, in Anaplastic Large-Cell Lymphoma and Inflammatory Myofibroblastic Tumor," Genes, Chromosomes & Cancer, 2002, 34:354-362.
Dorwald, F.A., Side Reactions in Organic Synthesis, 2005, Wiley: VCH, Weinheim, p. IX of Preface.
Druker et al., "Section 1: Chronic Myelogenous Leukemia," Cancer: Principles & Practice of Oncology, 7$^{th}$ Edition (DeVita et al., Eds.), 2121.
Faderl et al., "Section 3: Myelodysplastic Syndromes," Cancer: Principles & Practice of Oncology, 7$^{th}$ Edition (DeVita et al., Eds.), 2144.
Fine et al., "Section 2: Neoplasms of the Central Nervous System," Cancer: Principles & Practice of Oncology, 7$^{th}$ Edition (DeVita et al., Eds.), 1834-1887.
Fischer et al., "A Ki-1(CD30)-Positive Human Cell Line (Karpas 299) Established From a High-Grade Non-Hodgkin's Lymphoma, Showing a 2;5 Translocation and Rearrangement of the T-Cell Receptor β-Chain Gene," Blood, Jul. 1988, 72(1):234-240.
Galkin et al., "Identification of NVP-TAE684, a potent, selective and efficacious inhibitor of NPM-ALK," PNAS, Jan. 2, 2007, 104(1):270-275 (and Corrections published in PNAS, Feb. 6, 2007, 104(6):2024-2025).
Garbett et al., "Extending Nature's Leads: The Anticancer Agent Ellipticine," Curr. Med. Chem.—Anti-Cancer Agents, 2004, 4:149-172.
George et al., "Activating mutations in ALK provide a therapeutic target in neuroblastoma," Nature, 2008, 455:975-978.
Girouard et al., "Neurovascular coupling in the normal brain and in hypertension, stroke, and Alzheimer disease," Journal of Applied Physiology, 2006, 100:328-335.
Glick et al., "Treatment with atypical antipsychotics: new indications and new populations," Journal of Psychiatric Research, 2001, 35:187-191.
Goel et al., "Mice transgenic for BRAF V600E demonstrate phenotype affecting melanocyte and neural lineages," Proceedings of the American Association for Cancer Research, Apr. 2006, 47:#273.

(56) References Cited

OTHER PUBLICATIONS

Goodman & Gilman's, Chemotherapy of Neoplastic Diseases, The Pharmacological Basis of Therapeutics, Brunton et al., Eds., 2008, 11$^{th}$ Ed., 853-908.
Griffin et al., "Recurrent Involvement of 2p23 in Inflammatory Myofibroblastic Tumors," Cancer Research, Jun. 15, 1999, 59:2776-2780.
Herbst et al., "ALK Gene Products in Anaplastic Large Cell Lymphomas and Hodgkin's Disease," Blood, Sep. 1, 1995, 86(5):1694-1700.
Huang et al., "An in vivo model to study human GSTP1 polymorphisms in osteosarcoma," Proceedings of the American Association for Cancer Research, Apr. 2006, 47:#271.
Hübinger et al., "CD30-mediated cell cycle arrest associated with induced expression of p21$^{CIP1/WAF1}$ in the anaplastic large cell lymphoma cell line Karpas 299," Oncogene, 2001, 20:590-598.
Jazii et al., "Identification of squamous cell carcinoma associated proteins by proteomics and loss of beta tropomyosin expression in esophageal cancer," World J. Gastroenterol., Nov. 28, 2006, 12(44):7104-7112.
Kinoshita et al., "9-Substituted 6,6-Dimethyl-11-oxo-6,11-dihydro-5H-benzo[b]carbazoles as Highly Selective and Potent Anaplastic Lymphoma Kinase Inhibitors," J. Med. Chem., Sep. 22, 2011, 54(18):6286-6294.
Kinoshita et al., "Discovery of novel tetracyclic compounds as anaplastic lymphoma kinase inhibitors," Bioorganic & Medicinal Chemistry Letters, Apr. 8, 2011, 21(12):3788-3793.
Kirsch, Gilbert H., "Heterocyclic Analogues of Carbazole Alkaloids," Current Organic Chemistry, 2001, 5:507-518.
Kuppen et al., "Tumor structure and extracellular matrix as a possible barrier for therapeutic approaches using immune cells or adenoviruses in colorectal cancer," Histochem. Cell. Biol., 2001, 115:67-72.
Kuster, Bernhard, Ed., Kinase Inhibitors, Methods and Protocols, Methods in Molecular Biology, 2012, vol. 795, Chapter 1 by Fabbro et al., "Targeting Cancer with Small-Molecular-Weight Kinase Inhibitors."
Kwak et al., "Anaplastic Lymphoma Kinase Inhibition in Non-Small-Cell Lung Cancer," The New England Journal of Medicine, Oct. 28, 2010, 363(18):1693-1703.
Lamant et al., "Establishment of a novel anaplastic large-cell lymphoma-cell line (COST) from a 'small-cell variant' of ALCL," Leukemia, 2004, 18:1693-1698.
Lissoni et al., "Biotherapy with the pineal hormone melatonin plus aloe and myrrh tincture in untreatable metastatic cancer patients as an essence therapy of cancer," Cancer Therapy, 2009, 7:397-401.
Luo et al., "Principles of Cancer Therapy: Oncogene and Non-oncogene Addiction," Cell, Mar. 6, 2009, 136:823-837.
Mosse et al., "Identification of ALK as a major familial neuroblastoma predisposition gene," Nature, Oct. 16, 2008, 455:930-935, and Methods page.
National Cancer Institute, http://www.cancer.gov/, "A to Z List of Cancers," downloaded May 29, 2014, 22 pages.
O'Brien et al., "Section 2: Chronic Lymphoid Leukemias," Cancer: Principles & Practice of Oncology, 7$^{th}$ Edition (DeVita et al., Eds.), 2133.
O'Brien et al., "Vascular cognitive impairment," The Lancet Neurology, Feb. 2003, 2:89-98.
Pao et al., "EGF receptor gene mutations are common in lung cancers from 'never smokers' and are associated with sensitivity of tumors to gefitinib and erlotinib," PNAS, Sep. 7, 2004, 101(36):13306-13311.
Piva et al., "Ablation of oncogenic ALK is a viable therapeutic approach for anaplastic large-cell lymphomas," Blood, Jan. 2006, 107(2):689-697.
Rosenwald et al., "t(1;2)(q21;p23) and t(2;3)(p23;q21): Two Novel Variant Translocations of the t(2;5)(p23;q35) in Anaplastic Large Cell Lymphoma," Blood, Jul. 1, 1999, 94(1):362-364.
Sakamoto et al., "CH5424802, a Selective ALK Inhibitor Capable of Blocking the Resistant Gatekeeper Mutant," Cancer Cell, May 17, 2011, 19:679-690.
Scheinberg et al., "Section 2: Management of Acute Leukemias," Cancer: Principles & Practice of Oncology, 7$^{th}$ Edition (DeVita et al., Eds.), 2005, 2088, 2092.
Shah et al., "Current approaches in the treatment of Alzheimer's disease," Biomedicine & Pharmacotherapy, 2008, 62:199-207.
Shaw et al., "Targeting Anaplastic Lymphoma Kinase in Lung Cancer," Clinical Cancer Research, 2011, 17:2081-2086.
Shujuan, Wang, "The new insights on the diagnosis of malignant histiocytosis," Chinese Journal of Laboratory Medicine, Jan. 30, 2005, 28(1):14-16.
Silverman, Richard B., The Organic Chemistry of Drug Design and Drug Action, Second Ed., Elsevier Academic Press, Northwestern University, Evanston, Illinois, 2004, 29-31, table 2.2.
Soussi, Thierry, "p53 Antibodies in the Sera of Patients with Various Types of Cancer: A Review," Cancer Res., 2000, 60:1777-1788.
Stoica et al., "Identification of Anaplastic Lymphoma Kinase as a Receptor for the Growth Factor Pleiotrophin," J. Biol. Chem., May 18, 2001, 276(20:16772-16779.
Stoica et al., "Midkine Binds to Anaplastic Lymphoma Kinase (ALK) and Acts as a Growth Factor for Different Cell Types," J. Biol. Chem., Sep. 27, 2002, 277(39):35990-35998.
Wanner et al., "A convenient synthesis of 6-methylellipticine and 6-methylolivacine," Heterocycles, 1982, 19(12):2295-2300.
Wanner et al., "Inter- and Intramolecular Addition of Ester Anions to Nicotinium Salts, A Facile Approach to Nauclefine and Ellipticine Derivatives," Tetrahedron, Jan. 1, 1983, 3673-3681.
Wood et al., "Lack of the t(2;5) or Other Mutations Resulting in Expression of Anaplastic Lymphoma Kinase Catalytic Domain in CD30$^+$ Primary Cutaneous Lymphoproliferative Disorders and Hodgkin's Disease," Blood, Sep. 1, 1996, 88(5):1765-1770.
Zhao et al., "The progress of the research on anaplastic lymphoma kinase genetic abnormality of anaplastic large cell lymphoma," Foreign Medical Sciences (Section of Blood Transfusion and Hematology), Oct. 15, 2004, 27(5):403-406.
Bilsland et al., "Behavioral and Neurochemical Alterations in Mice Deficient in Anaplastic Lymphoma Kinase Suggest Therapeutic Potential for Psychiatric Indications," Neuropsychopharmacology, 2008, 33:685-700.
Seto et al., "CH5424802 (RO5424802) for patients with ALK-rearranged advanced non-small-cell lung cancer (AF-001JP study): a single-arm, open-label, phase 1-2 study," The Lancet Oncology, 2013, 14(7):590-598.
Soda et al., "Identification of the transforming EML4-ALK fusion gene in non-small-cell lung cancer," Nature, 2007, 448:561-566.

* cited by examiner

[FIG. 1]
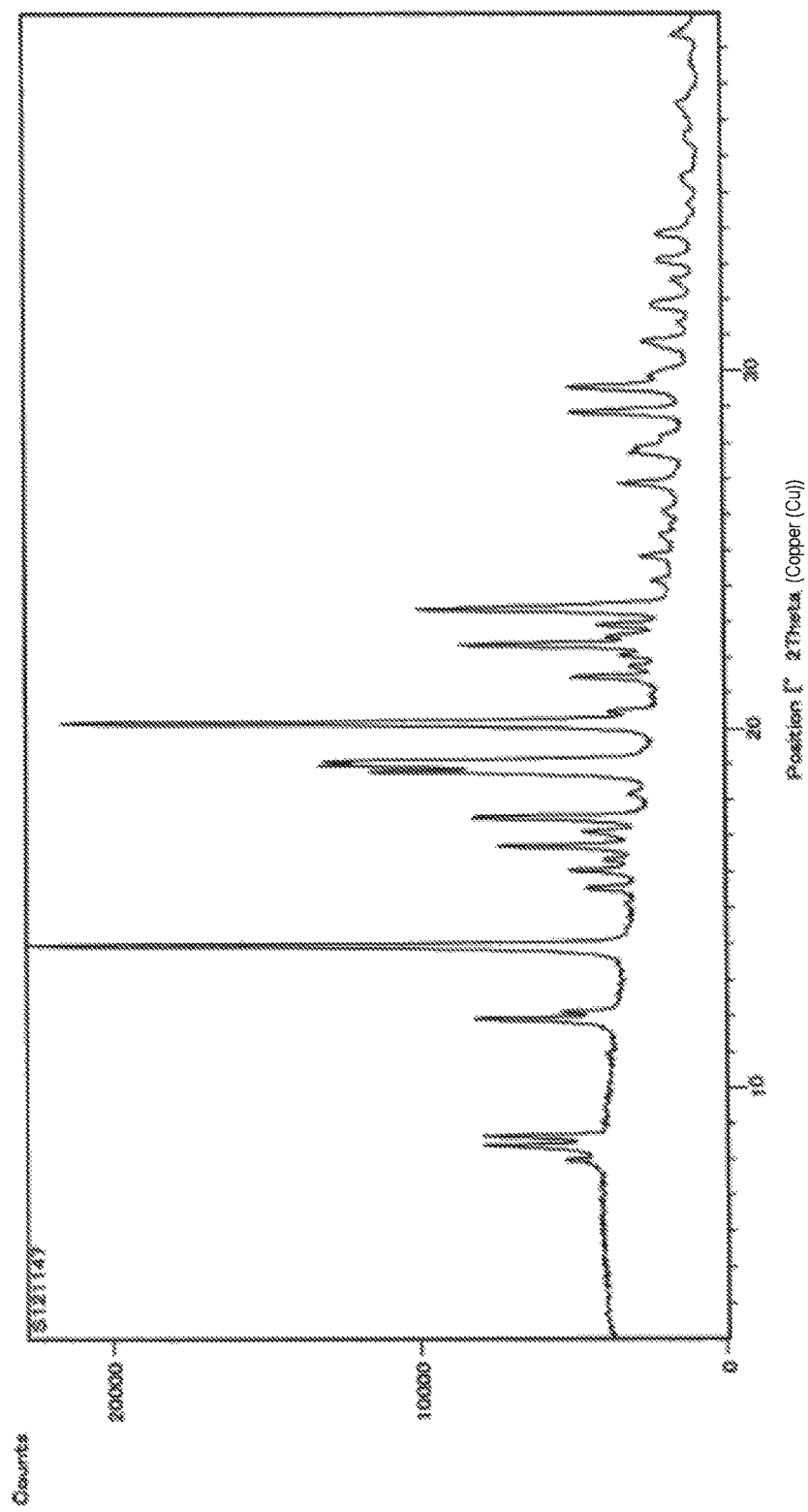

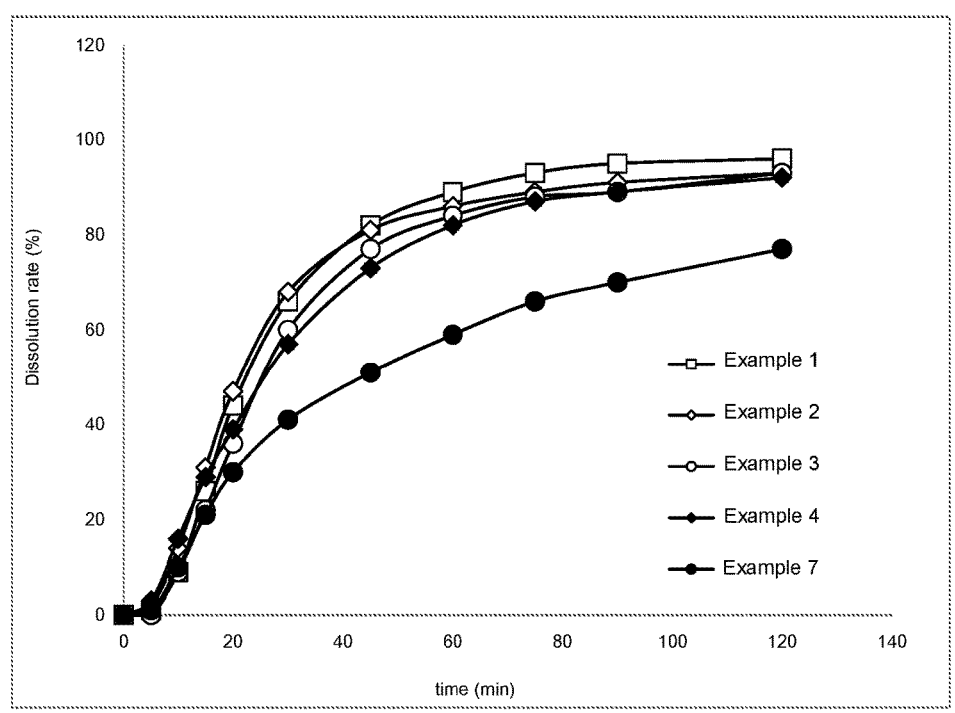
[FIG. 2]

[FIG. 3]
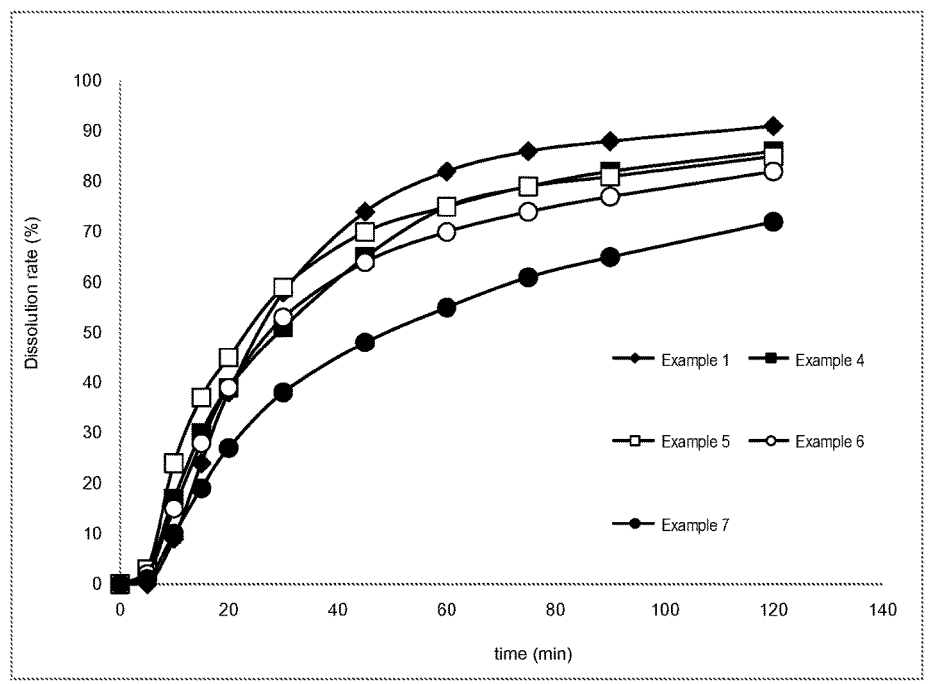

[FIG. 4]
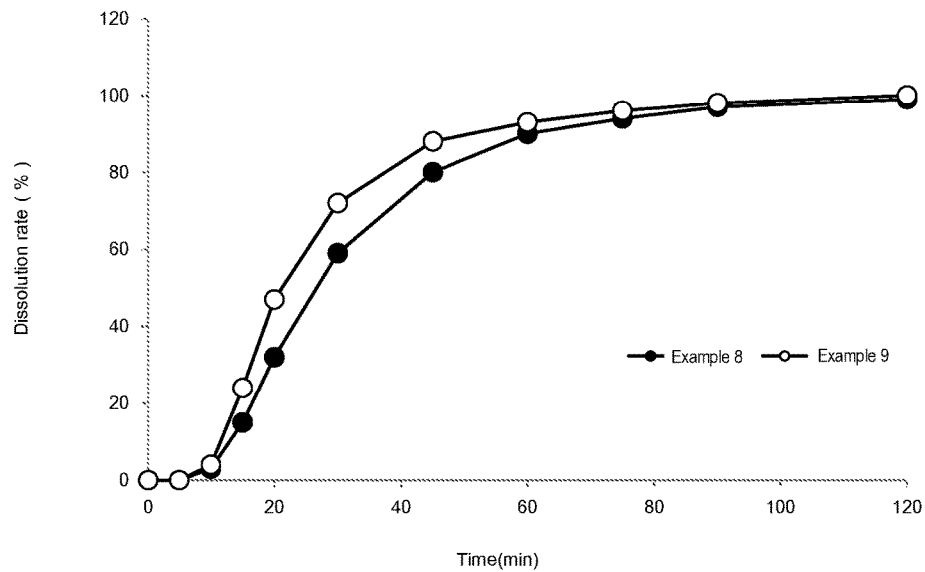
[FIG. 5]
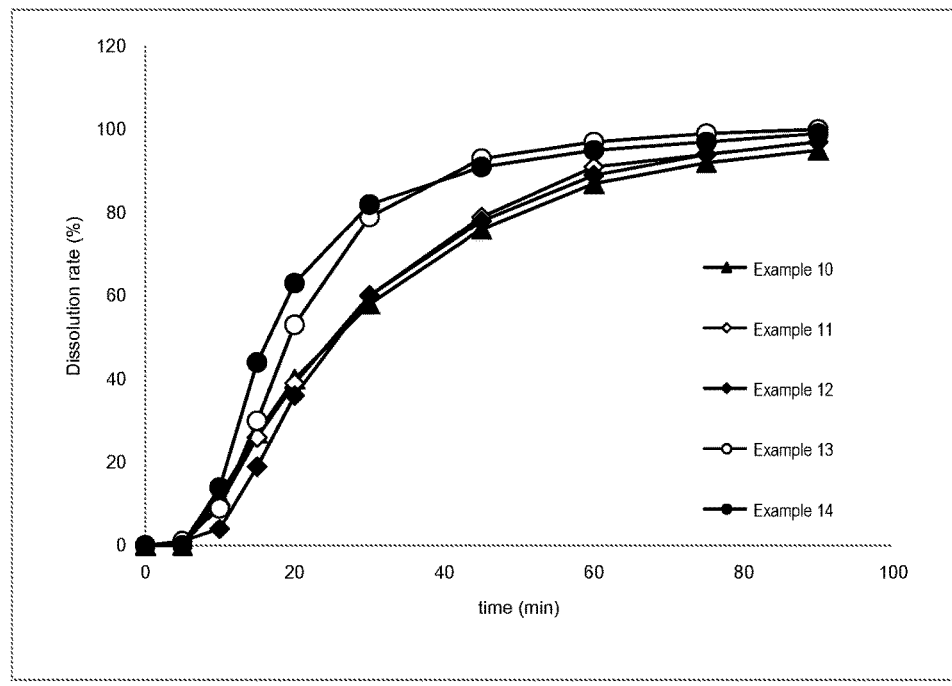

[FIG. 6-1]
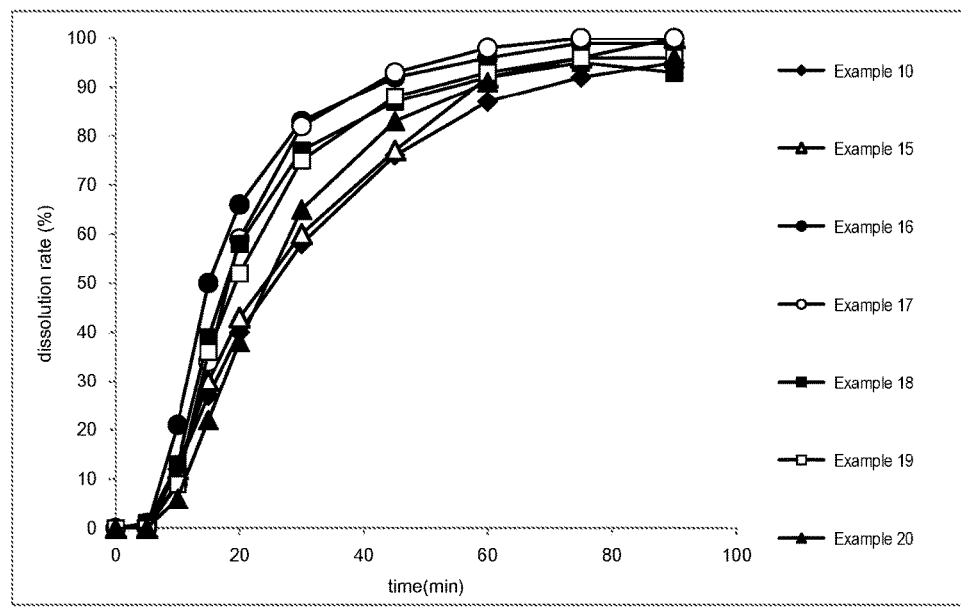
[FIG. 6-2]
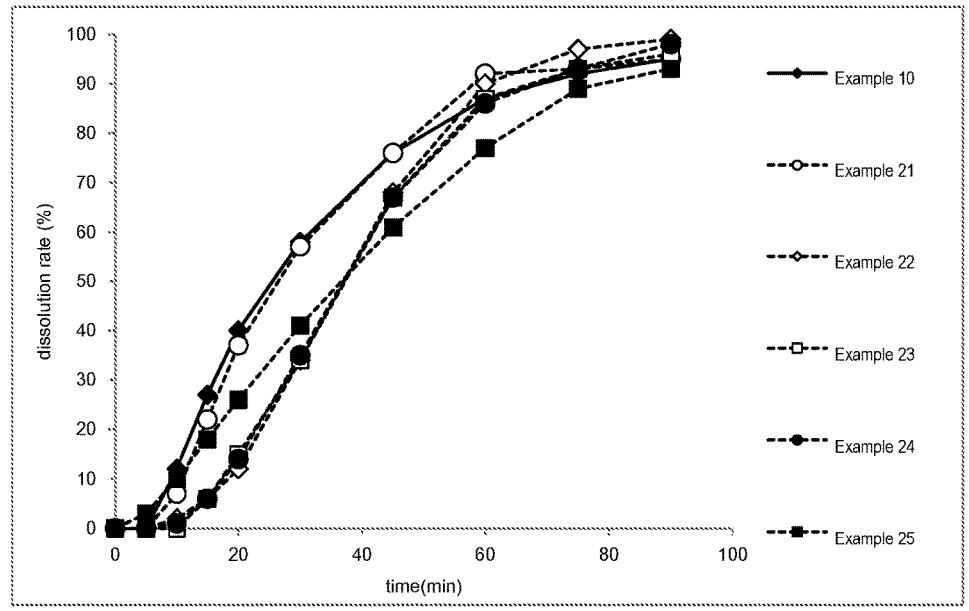

[FIG. 7]
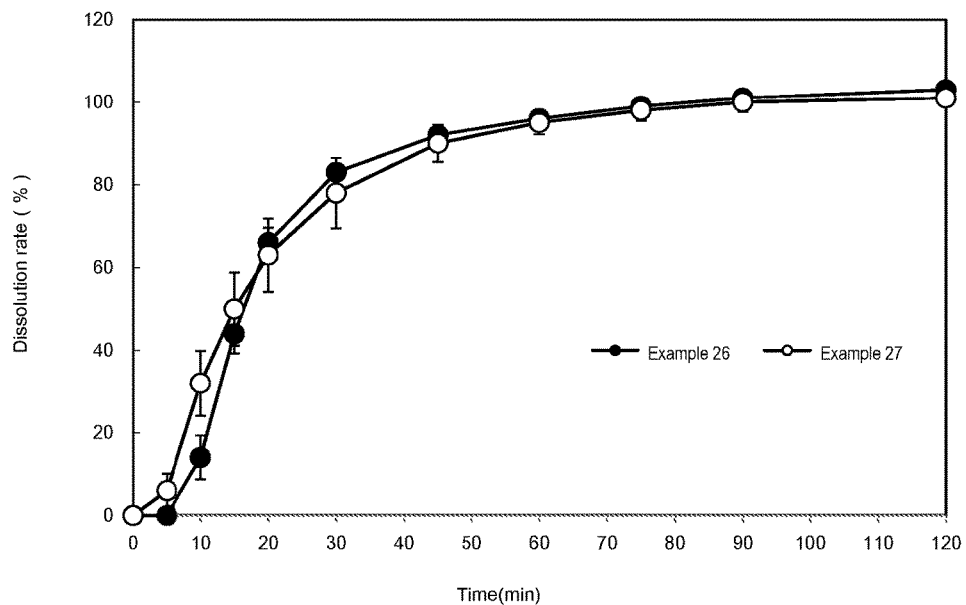
[FIG. 8]
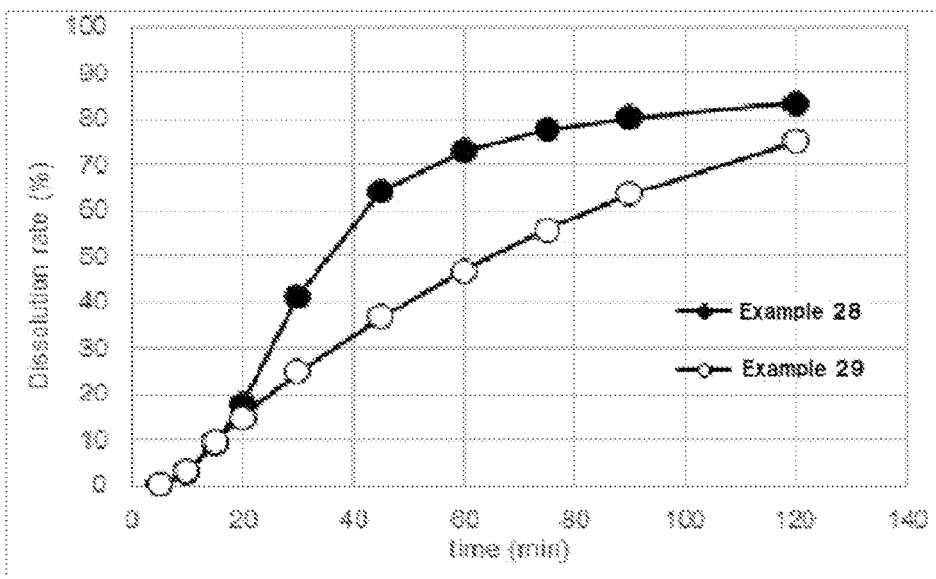

PREPARATION CONTAINING TETRACYCLIC COMPOUND AT HIGH DOSE

CROSS-REFERENCE TO RELATED APPLICATIONS

This application is a National Stage application of PCT/JP2015/062520, filed Apr. 24, 2015, which claims priority from Japanese application JP 2014-092101, filed Apr. 25, 2014.

TECHNICAL FIELD

The present invention relates to a pharmaceutical composition, particularly to an oral formulation of a tetracyclic compound, which is a substance having an ALK inhibitory action, and others.

BACKGROUND ART

Anaplastic Lymphoma Kinase (ALK) is a receptor tyrosine kinase belonging to an insulin receptor family (Non Patent Literature 1, Non Patent Literature 2). It is reported that abnormality of ALK gene causes the production of an abnormal kinase due to a fusion with another gene.

As diseases accompanying abnormality of ALK, for example, cancer and cancer metastasis (Non Patent Literature 1, Patent Literature 1); and depression and cognitive dysfunction (Non Patent Literature 2) are known. Providing an ALK inhibitor means providing an effective therapeutic and prophylactic agent for these diseases.

As a compound having an ALK inhibitory action, for example, a compound of the name of 9-ethyl-6,6-dimethyl-8-(4-morpholin-4-yl-piperidin-1-yl)-11-oxo-6,11-dihydro-5H-benzo[b]carbazole-3-carbonitrile represented by formula (I) is known (Patent Literature 2, Patent Literature 3, Patent Literature 4).

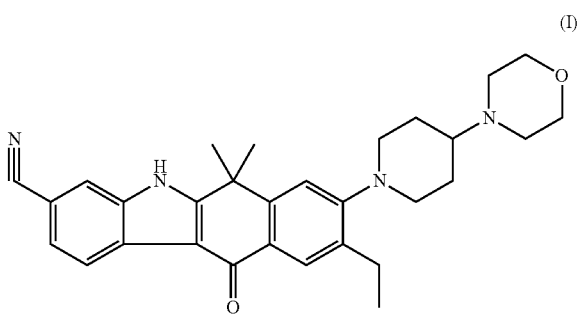 [SMILES: CCc1cc2c(cc1N1CCC(N3CCOCC3)CC1)C(C)(C)c1[nH]c3cc(C#N)ccc3c1C2=O]

(I)

Such a chemical compound is desirably developed as an orally-available dosage form as a medicinal agent; however, whether or not a medicinal agent can be developed as an oral formulation varies depending upon whether bioavailability of a medicinal substance is high or not. A factor influencing bioavailability is water solubility of a medicinal substance. Generally, compounds less soluble or insoluble in water are low in bioavailability if they are orally administered. Improving bioavailability of an active ingredient to thereby improve oral absorbability is important for the active ingredient to stably show its efficacy.

In the meantime, to increase the blood level of a medicinal substance less soluble or insoluble in water, thereby increasing a therapeutic effect, it is considered that the medicinal substance is used in a high dose. However, to improve patient's convenience, it is desired that the number of pills per administration and the administration times of an oral formulation are reduced. Accordingly, it is required to develop a formulation containing a large amount of a medicinal substance per unit.

A composition in which the compound represented by by formula (I) or a salt thereof is present together with a solubilizing agent has been reported (Patent Literature 4). For improving solubility and oral absorbability of a less water soluble or insoluble compound, a composition containing a component such as a steroid less soluble in water, a surfactant and an organic polymer and obtained by wet granulation in the presence of water, is reported (Patent Literature 5).

CITATION LIST

Patent Literature

[Patent Literature 1] JP2009100783 (A)
[Patent Literature 2] Japanese Patent No. 4588121
[Patent Literature 3] Japanese Patent No. 4918630
[Patent Literature 4] Japanese Patent Laid-Open No. 2012-126711
[Patent Literature 5] Japanese Patent Laid-Open No. 2008-280352

Non Patent Literature

[Non Patent Literature 1] Nature, vol. 448, pages 561-566, 2007
[Non Patent Literature 2] Neuropsychopharmacology, vol. 33, pages 685-700, 2008

SUMMARY OF INVENTION

The present inventors found, in a dissolution process of a formulation containing a large amount of the compound represented by formula (I) or a salt thereof, a phenomenon where the compound or a salt thereof aggregates and does not collapse, thus decreasing the solubility of the compound. The present inventors conducted intensive studies to solve the problem. As a result, they found that if granules formed of less water-soluble or insoluble compound represented by formula (I) or a salt thereof are formed and used together with a disintegrating agent, a formulation with satisfactory solubility containing a large amount of the compound represented by formula (I) or a salt thereof can be obtained.

The present inventors also found that a process for producing sodium lauryl sulfate serving as a surfactant influences solubility of a compound less soluble or insoluble in water.

The present inventors further conducted studies based on these findings and accomplished the present invention.

Means for Solving the Problems

More specifically, the present invention is as follows:

(1-1) A pharmaceutical composition comprising (i) a granule containing a compound represented by formula (I) or a salt thereof and (ii) a disintegrating agent.

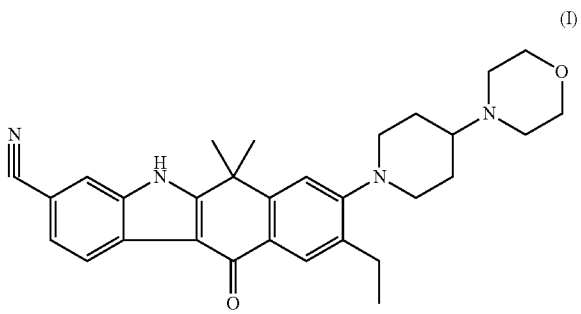 [SMILES: CCc1cc2c(cc1N1CCC(N3CCOCC3)CC1)C(C)(C)c1[nH]c3cc(C#N)ccc3c1C2=O]

(1-2) The composition according to (1-1), wherein the disintegrating agent (ii) is contained in an amount of 5 wt % or more based on the total amount of the composition.

(1-3) The composition according to (1-1) or (1-2), wherein the disintegrating agent (ii) is contained in an amount of 5 wt % or more and 30 wt % or less based on the total amount of the composition.

(1-4) The composition according to any of (1-1) to (1-3), wherein the disintegrating agent (ii) is contained in an amount of 7.5 wt % or more based on the total amount of the composition.

(1-5) The composition according to any of (1-1) to (1-4), wherein the disintegrating agent (ii) is contained in an amount of 7.5 wt % or more and 30 wt % or less based on the total amount of the composition.

(1-6) The composition according to any of (1-1) to (1-5), wherein the disintegrating agent (ii) is selected from sodium starch glycolate, low-substituted hydroxypropylcellulose, carmellose calcium, sodium hydrogen carbonate, pregelatinized starch, sodium chloride, corn starch, croscarmellose sodium, crystalline cellulose, silicic anhydride and carmellose.

(1-7) The composition according to any of (1-1) to (1-6), wherein the volume of the disintegrating agent (ii) becomes 2.5 times or more when adding 20 ml of 1st fluid for dissolution test defined in the Japanese Pharmacopenia $16^{th}$ edition is added to per 1.0 g of the disintegrating agent.

(1-8) The composition according to any of (1-1) to (1-6), wherein the disintegrating agent (ii) is selected from low-substituted hydroxypropylcellulose, carmellose calcium, sodium hydrogen carbonate and pregelatinized starch.

(1-9) The composition according to any of (1-1) to (1-8), wherein the disintegrating agent (ii) is carmellose calcium.

(1-10) The composition according to any of (1-1) to (1-9), wherein the granule contains a disintegrating agent therein.

(1-11) The composition according to any of (1-1) to (1-9), comprising the granule containing the compound (i) represented by formula (I) or a salt thereof and a disintegrating agent, and the disintegrating agent (ii).

(1-12) The composition according to (1-10) or (1-11), wherein the disintegrating agent contained in the granule is selected from sodium starch glycolate, low-substituted hydroxypropylcellulose, carmellose calcium, sodium hydrogen carbonate, pregelatinized starch, sodium chloride, corn starch, croscarmellose sodium, crystalline cellulose, silicic anhydride and carmellose.

(1-13) The composition according to either of (1-10) or (1-11), wherein the volume of the disintegrating agent contained in the granules becomes 2.5 times or more when adding 20 ml of 1st fluid for dissolution test defined in the Japanese Pharmacopenia $16^{th}$ edition to per 1.0 g of the disintegrating agent.

(1-14) The composition according to any of (1-1) to (1-13), wherein the disintegrating agent contained in the granule is selected from carmellose calcium, low-substituted hydroxypropylcellulose, sodium starch glycolate and pregelatinized starch.

(1-15) The composition according to any of (1-10) to (1-14), wherein the disintegrating agent contained in the granule is carmellose calcium.

(1-16) The composition according to any of (1-1) to (1-15), wherein the granule contains a solubilizing agent therein.

(1-17) The composition according to any of (1-1) to (1-15), comprising (i) a granule containing the compound represented by formula (I) or a salt thereof, a disintegrating agent and a solubilizing agent and (ii) the disintegrating agent.

(1-18) The composition according to (1-16) or (1-17), wherein the solubilizing agent is selected from the following group:

citric acid, hydroxypropylcellulose, hydroxypropylmethylcellulose, sodium stearyl fumarate, methacrylic acid copolymer LD, methylcellulose, sodium lauryl sulfate, polyoxyl 40 stearate, purified shellac, sodium dehydroacetate, fumaric acid, DL-malic acid, L-ascorbyl stearate, L-asparagine acid, adipic acid, aminoalkyl methacrylate copolymer E, propylene glycol alginate, casein, casein sodium, a carboxyvinyl polymer, carboxymethylethylcellulose, powdered agar, guar gum, succinic acid, copolyvidone, cellulose acetate phthalate, tartaric acid, dioctylsodium sulfosuccinate, zein, powdered skim milk, sorbitan trioleate, lactic acid, aluminum lactate, ascorbyl palmitate, hydroxyethylmethylcellulose, hydroxypropylmethylcelluloseacetate succinate, polyoxyethylene (105) polyoxypropylene (5) glycol, polyoxyethylene hydrogenated castor oil 60, polyoxyl 35 castor oil, poly(sodium 4-styrenesulfonate), polyvinylacetaldiethylamino acetate, polyvinyl alcohol, maleic acid, methacrylic acid copolymer S, lauromacrogol, sulfuric acid, aluminum sulfate, phosphoric acid, calcium dihydrogen phosphate, sodium dodecylbenzenesulfonate, a vinyl pyrrolidone-vinyl acetate copolymer, sodium lauroyl sarcosinate, acetyl tryptophan, sodium methyl sulfate, sodium ethyl sulfate, sodium butyl sulfate, sodium octyl sulfate, sodium decyl sulfate, sodium tetradecyl sulfate, sodium hexadecyl sulfate and sodium octadecyl sulfate.

(1-19) The composition according to any of (1-16) to (1-18), wherein the solubilizing agent is sodium lauryl sulfate.

(1-20) The composition according to (1-17), wherein sodium lauryl sulfate is obtained by crystallization.

(1-21) The composition according to any of (1-19) to (1-20), wherein the sodium lauryl sulfate is NIKKOL SLS.

(1-22) The composition according to (1-19) or (1-21), wherein sodium lauryl sulfate is a crystal of a ⅛ hydrate.

(1-23) The composition according to any of (1-16) to (1-22), wherein the weight ratio of the compound represented by formula (I) to the solubilizing agent is 100:2 to 100:60.

(1-24) The composition according to any of (1-16) to (1-23), wherein the weight ratio of the compound represented by formula (I) to the solubilizing agent is 100:2 to 100:30.

(1-25) The composition according to any of (1-1) to (1-24), wherein the granule contains a binder therein.

(1-26) The composition according to (1-25), wherein the binder is hydroxypropylcellulose.

(1-27) The composition according to any of (1-1) to (1-27), wherein the granule is obtained by wet granulation.

(1-28) The composition according to any of (1-1) to (1-27), wherein the granule has a mean particle diameter of 150 μm or more.

(1-29) The composition according to any of (1-1) to (1-28), wherein the granule has a mean particle diameter of 180 μm or more.

(1-30) The composition according to any of (1-1) to (1-29), wherein the granule has a mean particle diameter of 200 μm or more.

(1-31) The composition according to any of (1-1) to (1-30), wherein the granule has a mean particle diameter of 250 μm or more.

(1-32) The composition according to any of (1-1) to (1-31), wherein the granule has a mean particle diameter of 1 mm or less.

(1-33) The composition according to any of (1-1) to (1-32), wherein the bulk density of the granule is 0.5 g/ml or more and the tapping density is 0.6 g/ml or more.

(1-34) The composition according to any of (1-1) to (1-33), wherein a compound represented by formula (I) or a salt thereof is contained in an amount of 20 to 70 wt % in terms of the free form based on the total amount of the composition.

(1-35) The composition according to any of (1-1) to (1-34), wherein the compound represented by formula (I) or a salt thereof is contained in an amount of 35 to 60 wt % in terms of the free form based on the total amount of the composition.

(1-36) The composition according to any of (1-1) to (1-35), wherein the compound represented by formula (I) or a salt thereof is a monohydrochloride of the compound represented by formula (I).

(1-37) The composition according to (1-36), wherein the monohydrochloride of the compound represented by formula (I) is a crystal having a powder X-ray diffraction pattern wherein a peak is present at a diffraction angle (2θ) near 8.4°, 14.0°, 16.7°, 18.8° and 23.3°.

(1-38) A pharmaceutical formulation comprising the composition according to any of (1-1) to (1-37).

(1-39) The pharmaceutical formulation according to (1-38), being an oral formulation.

(1-40) The pharmaceutical formulation according to (1-39), wherein the oral formulation is a solid formulation.

(1-41) The pharmaceutical formulation according to (1-40), wherein the solid formulation is a tablet, a capsule or a granule formulation.

(1-42) A capsule charged with the composition according to any of (1-1) to (1-37).

(1-43) The formulation according to any of (1-38) to (1-42), wherein the compound represented by formula (I) or a salt thereof is contained in an amount of 60 mg to 240 mg in terms of the free form per unit formulation.

(1-44) The formulation according to any of (1-38) to (1-43), comprising the compound represented by formula (I) or a salt thereof in an amount of 140 mg to 190 mg per unit formulation.

(2-1) A pharmaceutical formulation comprising (i) a granule containing a compound represented by formula (I) or a salt thereof and (ii) a disintegrating agent.

(2-2) The formulation according to (2-1), comprising the disintegrating agent (ii) in an amount of 5 wt % or more based on the total amount of the formulation.

(2-3) The formulation according to (2-1) or (2-2), comprising the disintegrating agent (ii) in an amount of 5 wt % or more and 30 wt % or less based on the total amount of the formulation.

(2-4) The formulation according to (2-1) or (2-2), comprising the disintegrating agent (ii) in an amount of 7.5 wt % or more based on the total amount of the formulation.

(2-5) The formulation according to any of (2-1) to (2-4), comprising the disintegrating agent (ii) in an amount of 7.5 wt % or more 30 wt % or less based on the total amount of the formulation.

(2-6) The formulation according to any of (2-1) to (2-5), wherein the disintegrating agent (ii) is selected from sodium starch glycolate, low-substituted hydroxypropylcellulose, carmellose calcium, sodium hydrogen carbonate, pregelatinized starch, sodium chloride, corn starch, croscarmellose sodium, crystalline cellulose, silicic anhydride and carmellose.

(2-7) The formulation according to any of (2-1) to (2-6), wherein the disintegrating agent (ii) is selected from low-substituted hydroxypropylcellulose, carmellose calcium, sodium hydrogen carbonate and pregelatinized starch.

(2-8) The formulation according to any of (2-1) to (2-7), wherein the disintegrating agent (ii) is carmellose calcium.

(2-9) The formulation according to any of (2-1) to (2-8), wherein the granule contains a disintegrating agent therein.

(2-10) The formulation according to any of (2-1) to (2-9), (i) comprising a granule containing the compound represented by formula (I) or a salt thereof and a disintegrating agent, and (ii) the disintegrating agent.

(2-11) The formulation according to (2-10), wherein the disintegrating agent contained in the granule is selected from sodium starch glycolate, low-substituted hydroxypropylcellulose, carmellose calcium, sodium hydrogen carbonate, pregelatinized starch, sodium chloride, corn starch, croscarmellose sodium, crystalline cellulose, silicic anhydride and carmellose.

(2-12) The formulation according to any of (2-9) to (2-11), wherein the disintegrating agent contained in the granule is selected from carmellose calcium, low-substituted hydroxypropylcellulose and sodium starch glycolate.

(2-13) The formulation according to any of (2-9) to (2-12), wherein the disintegrating agent contained in the granule is carmellose calcium.

(2-14) The formulation according to any of (2-1) to (2-13), wherein the granule contains a solubilizing agent therein.

(2-15) The formulation according to any of (2-1) to (2-14) comprising (i) a granule containing the compound represented by formula (I) or a salt thereof, a disintegrating agent and a solubilizing agent and (ii) the disintegrating agent.

(2-16) The formulation according to (2-14) or (2-15), wherein the solubilizing agent is selected from the following group:

citric acid, hydroxypropylcellulose, hydroxypropylmethylcellulose, sodium stearyl fumarate, methacrylic acid copolymer LD, methylcellulose, sodium lauryl sulfate, polyoxyl 40 stearate, purified shellac, sodium dehydroacetate, fumaric acid, DL-malic acid, L-ascorbyl stearate, L-asparagine acid, adipic acid, aminoalkyl methacrylate copolymer E, propylene glycol alginate, casein, casein sodium, a carboxyvinyl polymer, carboxymethylethylcellulose, powdered agar, guar gum, succinic acid, copolyvidone, cellulose acetate phthalate, tartaric acid, dioctylsodium sulfosuccinate, zein, powdered skim milk, sorbitan trioleate, lactic acid, aluminum lactate, ascorbyl palmitate, hydroxyethylmethylcellulose, hydroxypropylmethylcelluloseacetate succinate, polyoxyethylene (105) polyoxypropylene (5) glycol, polyoxyethylene hydrogenated castor oil 60, polyoxyl 35 castor oil, poly(sodium 4-styrenesulfonate), polyvinylacetaldiethylamino acetate, polyvinyl alcohol, maleic acid, methacrylic acid copolymer S, lauromacrogol, sulfuric acid, aluminum sulfate, phosphoric acid, calcium dihydrogen phosphate, sodium dodecylbenzenesulfonate, a vinyl pyrrolidone-vinyl acetate copolymer, sodium lauroyl sarcosinate, acetyl tryptophan, sodium methyl sulfate, sodium ethyl sulfate, sodium butyl sulfate, sodium octyl sulfate, sodium decyl sulfate, sodium tetradecyl sulfate, sodium hexadecyl sulfate and sodium octadecyl sulfate.

(2-17) The formulation according to any of (2-14) to (2-16), wherein the solubilizing agent is sodium lauryl sulfate.

(2-18) The formulation according to (2-17), wherein sodium lauryl sulfate is obtained by crystallization.

(2-19) The formulation according to (2-17) or (2-18), wherein sodium lauryl sulfate is a crystal of a ⅛ hydrate.

(2-20) The formulation according to any of (2-14) to (2-19), wherein the weight ratio of the compound represented by formula (I) to the solubilizing agent is 100:2 to 100:60.

(2-21) The formulation according to any of (2-14) to (2-20), wherein the weight ratio of the compound represented by formula (I) to the solubilizing agent is 100:2 to 100:30.

(2-22) The formulation according to any of (2-1) to (2-21), wherein the granule is obtained by wet granulation.

(2-23) The formulation according to any of (2-1) to (2-22), wherein the granule has a mean particle diameter of 150 μm or more.

(2-24) The formulation according to any of (2-1) to (2-23), wherein the granule has a mean particle diameter of 180 μm or more.

(2-25) The formulation according to any of (2-1) to (2-24), wherein the granule has a mean particle diameter of 200 μm or more.

(2-26) The formulation according to any of (2-1) to (2-25), wherein the granule has a mean particle diameter of 250 μm or more.

(2-27) The formulation according to any of (2-1) to (2-26), wherein the granule has a mean particle diameter of 1 mm or less.

(2-28) The formulation according to any of (2-1) to (2-27), wherein the bulk density of the granule is 0.5 g/ml or more and the tapping density is 0.6 g/ml or more.

(2-29) The formulation according to any of (2-1) to (2-28), wherein the compound represented by formula (I) or a salt thereof is a monohydrochloride of the compound represented by formula (I).

(2-30) The formulation according to (2-29), wherein the monohydrochloride of the compound represented by formula (I) is a crystal having a powder X-ray diffraction pattern in which a peak is present at a diffraction angle (2θ) near 8.4°, 14.0°, 16.7°, 18.8° and 23.3°.

(2-31) The formulation according to any of (2-1) to (2-30), being an oral formulation.

(2-32) The formulation according to (2-31), wherein the oral formulation is a solid formulation.

(2-33) The formulation according to (2-32), wherein the solid formulation is a tablet, a capsule or a granule formulation.

(2-34) The formulation according to (2-33), wherein the solid formulation is a capsule.

(2-35) The formulation according to any of (2-1) to (2-34), wherein the compound represented by formula (I) or a salt thereof is contained in an amount of 20 to 70 wt % in terms of the free form based on the total amount of the formulation.

(2-36) The pharmaceutical formulation according to (2-34), wherein the compound represented by formula (I) or a salt thereof is contained in an amount of 35 to 60 wt % in terms of the free form based on the total amount of the components to be contained in the capsule.

(2-37) The formulation according to any of (2-1) to (2-36), wherein the compound represented by formula (I) or a salt thereof is contained in an amount of 60 mg to 240 mg in terms of the free form per unit formulation.

(2-38) The formulation according to any of (2-1) to (2-37), wherein the compound represented by formula (I) or a salt thereof is contained in an amount of 140 mg to 190 mg in terms of the free form per unit formulation.

(3-1) A method for producing a formulation improved in solubility of a compound represented by formula (I) or a salt thereof, comprising (i) granulating a granule containing a compound represented by formula (I) or a salt thereof and (ii) blending a disintegrating agent and optionally other additives as external additives.

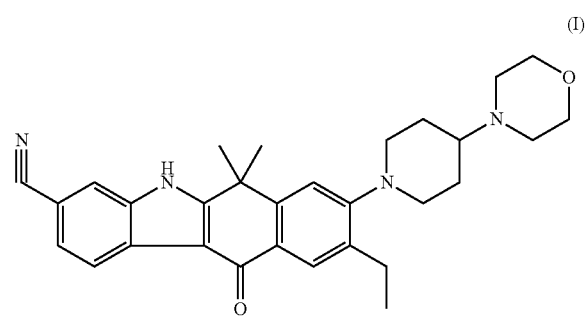 [SMILES: CCc1cc2c(cc1N1CCC(N3CCOCC3)CC1)C(C)(C)c1[nH]c3cc(C#N)ccc3c1C2=O]

(3-2) The method according to (3-1), wherein the disintegrating agent (ii) is selected from sodium starch glycolate, low-substituted hydroxypropylcellulose, carmellose calcium, sodium hydrogen carbonate, pregelatinized starch, sodium chloride, corn starch, croscarmellose sodium, crystalline cellulose, silicic anhydride and carmellose.

(3-3) The method according to (3-1) or (3-2), wherein the volume of the disintegrating agent (ii) becomes 2.5 times or more when adding 20 ml of 1st fluid for dissolution test defined in the Japanese Pharmacopenia $16^{th}$ edition to per 1.0 g of the disintegrating agent.

(3-4) The method according to any of (3-1) to (3-3), wherein the disintegrating agent (ii) is contained in an amount of 7.5 wt % or more and 30 wt % or less based on the total amount of the formulation.

(3-5) The method according to any of (3-1) to (3-4), wherein the granule has a mean particle diameter of 150 μm or more and 1 mm or less.

(3-6) The method according to any of (3-1) to (3-5), wherein the granule has a mean particle diameter of 180 μm or more and 1 mm or less.

(3-7) The method according to any of (3-1) to (3-6), wherein the bulk density of the granule is 0.5 g/ml or more and the tapping density is 0.6 g/ml or more.

(3-8) The method according to any of (3-1) to (3-7), wherein the granule (i) contains a disintegrating agent therein.

(3-9) The method according to (3-8), wherein the disintegrating agent contained in the granule is selected from sodium starch glycolate, low-substituted hydroxypropylcellulose, carmellose calcium, sodium hydrogen carbonate, pregelatinized starch, sodium chloride, corn starch, croscarmellose sodium, crystalline cellulose, silicic anhydride and carmellose.

(3-10) The method according to (3-8) or (3-9), wherein the volume of the disintegrating agent (ii) becomes 2.5 times or more when adding 20 ml of 1st fluid for dissolution test defined in the Japanese Pharmacopenia $16^{th}$ edition to per 1.0 g of disintegrating agent.

(3-11) The method according to any of (3-1) to (3-10), wherein the granule contains a solubilizing agent therein.

(3-12) The method according to any of (3-1) to (3-11), wherein the solubilizing agent is selected from the following group:

citric acid, hydroxypropylcellulose, hydroxypropylmethylcellulose, sodium stearyl fumarate, methacrylic acid copolymer LD, methylcellulose, sodium lauryl sulfate, polyoxyl 40 stearate, purified shellac, sodium dehydroacetate, fumaric acid, DL-malic acid, L-ascorbyl stearate, L-asparagine acid, adipic acid, aminoalkyl methacrylate copolymer E, propylene glycol alginate, casein, casein sodium, a carboxyvinyl polymer, carboxymethylethylcellulose, powdered agar, guar gum, succinic acid, copolyvidone, cellulose acetate phthalate, tartaric acid, dioctylsodium sulfosuccinate, zein, powdered skim milk, sorbitan trioleate, lactic acid, aluminum lactate, ascorbyl palmitate, hydroxyethylmethylcellulose, hydroxypropylmethylcelluloseacetate succinate, polyoxyethylene (105) polyoxypropylene (5) glycol, polyoxyethylene hydrogenated castor oil 60, polyoxyl 35 castor oil, poly(sodium 4-styrenesulfonate), polyvinylacetaldiethylamino acetate, polyvinyl alcohol, maleic acid, methacrylic acid copolymer S, lauromacrogol, sulfuric acid, aluminum sulfate, phosphoric acid, calcium dihydrogen phosphate, sodium dodecylbenzenesulfonate, a vinyl pyrrolidone-vinyl acetate copolymer, sodium lauroyl sarcosinate, acetyl tryptophan, sodium methyl sulfate, sodium ethyl sulfate, sodium butyl sulfate, sodium octyl sulfate, sodium decyl sulfate, sodium tetradecyl sulfate, sodium hexadecyl sulfate and sodium octadecyl sulfate.

(3-13) The method according to any of (3-1) to (3-12), wherein the solubilizing agent is sodium lauryl sulfate obtained by crystallization.

(3-14) The method according to any of (3-11) to (3-13), wherein the sodium lauryl sulfate is NIKKOL SLS.

(3-15) The method according to any of (3-11) to (3-14), wherein a weight ratio of the compound represented by formula (I) to the solubilizing agent is 100:2 to 100:60.

(3-16) The method according to any of (3-1) to (3-15), wherein the granule contains a binder therein.

(3-17) The method according to (3-15), wherein the binder is hydroxypropylcellulose.

(3-18) The method according to any of (3-1) to (3-17), wherein the compound represented by formula (I) or a salt thereof is contained in an amount of 20 to 70 wt % in terms of the free form based on the total amount of the formulation.

(3-19) The method according to any of (3-1) to (3-18), wherein the compound represented by formula (I) or a salt thereof is contained in an amount of 60 mg to 240 mg in terms of the free form per unit formulation.

(3-20) The method according to any of (3-1) to (3-19), wherein the dissolution rate of the compound represented by formula (I) or a salt thereof is 65% or more at 75 minutes after initiation of a dissolution test at 37° C.

(3-21) A formulation produced by the process according to any one of (3-1) to (3-20).

BRIEF DESCRIPTION OF DRAWINGS

FIG. 1 is a graph showing measurement results of powder X-ray diffraction of Form I crystal.

FIG. 2 is a graph showing dissolution profiles of Examples 1 to 4 and 7 in the dissolution test by the paddle method (100 rotations/minute) according to the Japanese pharmacopeia.

FIG. 3 is a graph showing dissolution profiles of Examples 1 and 4 to 7 in the dissolution test by the paddle method (100 rotations/minute) according to the Japanese pharmacopeia.

FIG. 4 is a graph showing dissolution profiles of Examples 8 and 9 in the dissolution test by the paddle method (100 rotations/minute) according to the Japanese pharmacopeia.

FIG. 5 is a graph showing dissolution profiles of Examples 10 to 14 in the dissolution test by the paddle method (100 rotations/minute) according to the Japanese pharmacopeia.

FIG. 6 is a graph showing dissolution profiles of Examples 10 and 15 to 20 (FIG. 6-1) and Examples 10 and 21 to 25 (FIG. 6-2) in the dissolution test by the paddle method (100 rotations/minute) according to the Japanese pharmacopeia.

FIG. 7 is a graph showing dissolution profiles of Examples 26 and 27 in the dissolution test by the paddle method (100 rotations/minute) according to the Japanese pharmacopeia.

FIG. 8 is a graph showing dissolution profiles of Examples 28 and 29 in the dissolution test by the paddle method (100 rotations/minute) according to the Japanese pharmacopeia.

MODE FOR CARRYING OUT THE INVENTION

In the present invention, the "granule(s)" refers to grain(s) having almost a uniform shape and size, which is obtained by granulating a raw material in the state of powder, aggregate, solution or molten liquid by means of e.g., wet granulation, dry granulation or heat granulation. As the equipment used for granule preparation, a high-shear granulator is preferable to a mortar from the perspective of elution. Note that the granules may be changed in size and shape in a process (e.g., tablet making step) for obtaining a formulation of the present invention.

The mean particle diameter of granules of the present invention is, for example, 150 μm or more, preferably, 180 μm or more, more preferably, 200 μm or more and further preferably 250 μm or more, and especially preferably, 300 μm or more. The upper limit of the mean particle diameter of granules, which is not particularly limited, is, for example, 1 mm.

The mean particle diameter is obtained by performing following steps: (i) feed a granulated substance sampled onto the top of the stacked sieves different in mesh size (mesh size: 850, 500, 355, 250, 180, 106, 75, 53, 0 μm), (ii) shake the sieves for 3 minutes, (iii) measure the weights of granulated substances remaining on the individual sieves, (iv) calculate the particle diameter of the granules which have a cumulative percentage of 50% by means of approximation of logarithmic normal distribution from the mesh size of the sieve and cumulative weight percentage undersize. If the granulated substance contains more than 10% by weight of granules which have a particle diameter of larger than 850 μm, the mean particle diameter is obtained by calculating a particle diameter of the granule which has a cumulative percentage of 50% by means of approximation of Rosin-Rammler distribution from the mesh size of the sieve and cumulative weight percentage oversize.

The granule of the present invention preferably have a bulk density of 0.5 g/ml or more and a tapping density of 0.6 g/ml or more, and more preferably have a bulk density of 0.6 g/ml or more and a tapping density of 0.7 g/ml or more. Upper limit of a bulk density and a tapping density are not limited, but preferably 1.0 g/ml. Bulk density and tapping density are measured according to the test methods described in the Japanese Pharmacopoeia 16$^{th}$ edition.

In the present invention, the "wet granulation" refers to a method for granulating powder while adding, spraying or spreading water or a solution mixture of water and e.g., alcohol serving as a granulation solvent.

The size of particle diameter, of granules can be adjusted by increasing or decreasing the amount of water or solution mixture used during the wet granulation process.

The pharmaceutical composition or pharmaceutical formulation of the present invention is a composition or a formulation comprising (i) a granule containing a compound represented by formula (I) or a salt thereof and (ii) a disintegrating agent and having a satisfactory solubility. The disintegrating agent (ii) refers to one to be added as an external additive. The "disintegrating agent" in the present invention is a component facilitating rapid disintegration of a solid formulation orally taken. In the present invention, the "external additive" and "external component" refer to additives externally added to granules. As the additive, other than the disintegrating agent, additives such as a lubricant and a fluidizer may be further optionally added.

Examples of the disintegrating agent (ii) include sodium starch glycolate, low-substituted hydroxypropylcellulose, carmellose calcium, sodium hydrogen carbonate, pregelatinized starch, sodium chloride, corn starch, croscarmellose sodium, crystalline cellulose, silicic anhydride, carmellose, etc. The volume of disintegrating agent becomes preferably more than 2.5 times, and more preferably, more than 5 times when adding 20 ml of 1st fluid for dissolution test defined in the Japanese Pharmacopenia 16$^{th}$ edition to per 1.0 g of the disintegrating agent. Examples of preferable disintegrating agents include, e.g., low-substituted hydroxypropylcellulose, carmellose calcium, sodium hydrogen carbonate, pregelatinized starch, etc.

The amount of the disintegrating agent (ii) is, for example, 5 wt % or more, preferably, 7.5 wt % or more, further preferably 8.5 wt % or more, and especially preferably 10 wt % or more based on the total amount of the composition or formulation of the present invention. The upper limit of the amount used, which is not particularly limited, is, for example, 30 wt %, 25 wt %. Note that, if the formulation of the present invention is a formulation having a coating film such as a capsule and a coated tablet, the amount used refers to the amount used based on the total amount of the components to be covered with the coating film (or the total amount of the components to be put in a capsule, or the total amount of the components covered with a coating film).

In the present invention, the granule (i) may contain various types of additives other than the compound represented by formula (I) or a salt thereof.

In one aspect of the present invention, the granule (i) contains a compound represented by formula (I) or a salt thereof, a disintegrating agent, a solubilizing agent, an excipient and a binder. The granule may further contain one or more additives selected from a lubricant, a coating agent, a stabilizer, a flavoring agent and a diluent.

Examples of the disintegrating agent to be contained in the granule (i) include sodium starch glycolate, low-substituted hydroxypropylcellulose, carmellose calcium, sodium hydrogen carbonate, pregelatinized starch, sodium chloride, corn starch, croscarmellose sodium, crystalline cellulose, silicic anhydride and carmellose. The preferable disintegrating agent is such that the volume of the disintegrating agent becomes preferably more than 2.5 times, and more preferably, more than 5 times when adding 20 ml of 1st fluid for dissolution test defined in the Japanese Pharmacopenia 16$^{th}$ edition to per 1.0 g of the disintegrating agent. Examples of preferable dissolusion agent include low-substituted hydroxypropylcellulose, carmellose calcium, sodium starch glycolate, and pregelatinized starch and so on.

The "solubilizing agent" contained in the granule (i) of the present invention refers to a surfactant, an organic polymer or a pH modifier.

The "surfactant" refers to a substance having a hydrophilic group together with a hydrophobic group in a molecule. Examples of the surfactant include an ionic surfactant and a nonionic surfactant.

The ionic surfactant refers to an ionic surfactant which ionizes into ions (charged atoms or atomic groups) when dissolved in water. The ionic surfactant is further classified into an anionic surfactant, a cationic surfactant and an amphoteric surfactant depending upon the charge of the ion to be produced. In the present invention, a nonionic surfactant and an anionic surfactant are preferable.

Examples of the nonionic surfactant include sugar ester surfactants such as a sorbitan fatty acid ester (C12-18), a POE sorbitan fatty acid ester (C12-18) and sucrose fatty acid ester; fatty acid ester surfactants such as a POE fatty acid ester (C12-18), a POE resin acid ester and a POE fatty acid diester (C12-18); alcohol based surfactants such as a POE alkyl ether (C12-18); alkyl phenol surfactants such as a POE alkyl (C8-12) phenyl ether, a POE dialkyl (C8-12) phenyl ether and a POE alkyl (C8-12) phenyl ether formalin condensate; polyoxyethylene-polyoxypropylene block polymer surfactants such as a polyoxyethylene-polyoxypropylene block polymer and an alkyl (C12-18) polyoxyethylene-polyoxypropylene block polymer ether; alkylamine surfactants such as a POE alkylamine (C12-18) and a POE fatty acid amide (C12-18); bisphenol surfactants such as a POE fatty acid bisphenyl ether; polycyclic aromatic surfactants such as a POA benzylphenyl (or phenylphenyl) ether and a POA styrylphenyl (or phenylphenyl) ether; POE ether and ester type silicon and fluorine surfactants; and vegetable oil surfactants such as POE castor oil and POE hydrogenated castor oil. Preferably, e.g., polyoxyl 40 stearate, sorbitan trioleate, polyoxyethylene (105) polyoxypropylene (5) glycol, polyoxyethylene hydrogenated castor oil 60, polyoxyl 35 castor oil and lauromacrogol are mentioned.

Examples of the anionic surfactant include sulfate surfactants such as an alkyl sulfate (C12-18, Na, NH$_4$, alkanolamine), a POE alkyl ether sulfate (C12-18, Na, NH$_4$, alkanolamine), a POE alkyl phenyl ether sulfate (C12-18, NH$_4$, alkanolamine, Ca), a POE benzyl (or styryl) phenyl (or phenylphenyl) ether sulfate (Na, NH$_4$, alkanolamine), a polyoxyethylene and a polyoxypropylene block polymer sulfate (Na, NH$_4$, alkanolamine); sulfonate surfactants such as a paraffin (alkane) sulfonate (C12-22, Na, Ca, alkanolamine), an AOS (C14-16, Na, alkanolamine), a dialkyl sulfosuccinate (C8-12, Na, Ca, Mg), an alkylbenzene sulfonate (C12, Na, Ca, Mg, NH$_4$, alkylamine, alkanol, amine, cyclohexylamine), a mono or dialkyl (C3-6) naphthalene sulfonate (Na, NH4, alkanolamine, Ca, Mg), a naphthalene sulfonate-formalin condensate (Na, NH$_4$), an alkyl (C8-12) diphenyl ether disulfonate (Na, NH$_4$), a lignin sulfonate (Na, Ca), a POE alkyl (C8-12) phenyl ether sulfonate (Na) and a POE alkyl (C12-18) ether sulfosuccinic acid half ester (Na); carboxylic acid surfactants such as a fatty acid salt (C12-18, Na, K, NH$_4$, alkanolamine), a N-methyl-fatty acid sarcosinate (C12-18, Na) and a resinate (Na, K); and phosphate surfactants such as a POE alkyl (C12-18) ether phosphate (Na, alkanolamine), a POE mono or dialkyl (C8-12) phenyl ether phosphate (Na, alkanolamine), a POE benzylated (or styrylated) phenyl (or phenylphenyl) ether phosphate (Na, alkanolamine), a polyoxyethylene-polyoxypropylene block polymer (Na, alkanolamine), a phosphatidylcholine-phosphatidyl ethanol imine (lecithin) and an alkyl (C8-12) phosphate. Preferably, e.g., monoalkyl sulfates such as sodium lauryl sulfate, sodium tetradecyl sulfate, sodium hexadecyl sulfate and sodium octadecyl sulfate, dioctylsodium sulfosuccinate, sodium lauroyl sarcosinate and sodium dodecylbenzenesulfonate are mentioned.

The organic polymer refers to a substance having carbon as a main skeleton and a molecular weight of 10,000 or more. Examples of the organic polymer include proteins and polysaccharides derived from animals and plants, and synthetic resins.

Specific examples of the organic polymer include polysaccharides such as hydroxypropylcellulose (hereinafter also referred to as HPC), hydroxypropylmethylcellulose, methylcellulose, propylene glycol alginate, powdered agar, guar gum, zein and hydroxyethylmethylcellulose; synthetic resins such as a carboxyvinyl polymer, a polyvinyl alcohol, a vinyl acetate resin and a sodium polystyrene sulfonate; and phosphoproteins such as casein and casein sodium.

Of the organic polymers, a polymer having a solubility to water of 1 g/100 g or more is called a water-soluble polymer. Specific examples thereof include hydroxypropylcellulose, hydroxypropylmethylcellulose, methylcellulose, propylene glycol alginate, casein sodium, a carboxyvinyl polymer, powdered agar, guar gum, copolyvidone, hydroxyethylmethylcellulose and a polyvinyl alcohol.

Of the organic polymers, a polymer dissolved in acidic conditions (pH of the gastric juice, 1.2 to 3.5) is called a gastrosoluble polymer; whereas a polymer quickly dissolved in the intestinal pH (6 to 8) is called an enteric polymer. Examples of the gastrosoluble polymer include an aminoalkyl methacrylate copolymer E and a polyvinyl acetal diethylamino acetate. Examples of the enteric polymer include a methacrylic acid copolymer LD (emulsion), methacrylic acid copolymer S, purified shellac, carboxymethylethylcellulose, cellulose acetate phthalate (cellaphate), hydroxypropylmethylcellulose acetate succinate, casein and zein.

The "pH modifier" refers to a substance controlling pH of a solution by adding an acid agent or an alkali agent to improve solubility of a less water soluble or insoluble compound. The pH modifier is appropriately selected in accordance with the feature of a substance to be solubilized. For example, in the case of a basic and less water soluble or insoluble compound, the solubility may be often improved if an acid agent is added to change pH to be acidic.

Examples of the pH modifier include adipic acid, citric acid, trisodium citrate, gluconic acid, sodium gluconate, gluconodelta lactone, potassium gluconate, succinic acid, monosodium succinate, disodium succinate, sodium acetate, L-tartaric acid, L-potassium hydrogen tartrate, L-sodium tartrate, DL-tartaric acid, DL-potassium hydrogen tartrate, DL-sodium tartrate, sodium hydrogen carbonate, potassium carbonate (anhydrous), sodium carbonate, carbon dioxide, lactic acid, sodium lactate, glacial acetic acid, disodium dihydrogen pyrophosphate, fumaric acid, monosodium fumarate, DL-malic acid, DL-sodium malate, phosphoric acid, potassium dihydrogen phosphate, sodium dihydrogen phosphate, dipotassium hydrogen phosphate and disodium hydrogen phosphate.

Preferably, the pH modifier is acid agents such as adipic acid, citric acid, gluconic acid, gluconodelta lactone, succinic acid, L-tartaric acid, DL-tartaric acid, carbon dioxide, lactic acid, glacial acetic acid, fumaric acid, DL-malic acid and phosphoric acid may be mentioned.

In the present invention, two types or more solubilizing agents may be used by combining them in an appropriate ratio.

In the present invention, preferable solubilizing agents are as follows:

citric acid, hydroxypropylcellulose, hydroxypropylmethylcellulose, sodium stearyl fumarate, methacrylic acid copolymer LD, methylcellulose, sodium lauryl sulfate, polyoxyl 40 stearate, purified shellac, sodium dehydroacetate, fumaric acid, DL-malic acid, L-ascorbyl stearate, L-asparagine acid, adipic acid, aminoalkyl methacrylate copolymer E, propylene glycol alginate, casein, casein sodium, a carboxyvinyl polymer, carboxymethylethylcellulose, powdered agar, guar gum, succinic acid, copolyvidone, cellulose acetate phthalate, tartaric acid, dioctylsodium sulfosuccinate, zein, powdered skim milk, sorbitan trioleate, lactic acid, aluminum lactate, ascorbyl palmitate, hydroxyethylmethylcellulose, hydroxypropylmethylcellulose acetate succinate, polyoxyethylene (105) polyoxypropylene (5) glycol, polyoxyethylene hydrogenated castor oil 60, polyoxyl 35 castor oil, poly(sodium 4-styrenesulfonate), polyvinyl acetal diethylamino acetate, polyvinyl alcohol, maleic acid, methacrylic acid copolymer S, lauromacrogol, sulfuric acid, aluminum sulfate, phosphoric acid, calcium dihydrogen phosphate, sodium dodecylbenzenesulfonate, a vinyl pyrrolidone-vinyl acetate copolymer, sodium lauroyl sarcosinate, acetyl tryptophan, sodium methyl sulfate, sodium ethyl sulfate, sodium butyl sulfate, sodium octyl sulfate, sodium decyl sulfate, sodium tetradecyl sulfate, sodium hexadecyl sulfate and sodium octadecyl sulfate.

In the present invention, more preferable solubilizing agents are as follows:

citric acid, hydroxypropylcellulose, hydroxypropylmethylcellulose, methacrylic acid copolymer LD, methylcellulose, sodium lauryl sulfate, purified shellac, sodium dehydroacetate, fumaric acid, DL-malic acid, L-ascorbyl stearate, L-asparagine acid, adipic acid, propylene glycol alginate, casein, casein sodium, carboxymethylethylcellulose, succinic acid, copolyvidone, dioctylsodium sulfosuccinate, lactic acid, aluminum lactate, ascorbyl palmitate, hydroxyethylmethylcellulose, hydroxypropylmethylcellulose acetate succinate, polyoxyethylene hydrogenated castor oil 60, polyoxyl 35 castor oil, poly(sodium 4-styrenesulfonate), polyvinyl acetal diethylamino acetate, polyvinyl alcohol, methacrylic acid copolymer S, lauromacrogol, sulfuric acid, aluminum sulfate, sodium dodecylbenzenesulfonate, a vinyl pyrrolidone-vinyl acetate copolymer, acetyl tryptophan, sodium decyl sulfate, sodium tetradecyl sulfate and sodium octadecyl sulfate.

In the present invention, further preferable solubilizing agents are as follows:

citric acid, hydroxypropylcellulose, hydroxypropylmethylcellulose, methacrylic acid copolymer LD, methylcellulose, sodium lauryl sulfate, purified shellac, sodium dehydroacetate, fumaric acid, DL-malic acid, L-asparagine acid, adipic acid, propylene glycol alginate, casein sodium, carboxymethylethylcellulose, succinic acid, copolyvidone, dioctylsodium sulfosuccinate, lactic acid, aluminum lactate, hydroxyethylmethylcellulose, hydroxypropylmethylcellulose acetate succinate, poly(sodium 4-styrenesulfonate), polyvinyl acetal diethylamino acetate, methacrylic acid copolymer S, sulfuric acid, aluminum sulfate and a vinyl pyrrolidone-vinyl acetate copolymer.

The content of the solubilizing agent in the composition or formulation of the present invention is preferably 2 wt % to 60 wt %, more preferably, 20-60 wt %, based on the compound represented by formula (I) (free form).

In the present invention, when sodium lauryl sulfate is used, it is more preferable to obtain a crystal thereof by crystallization rather than spray dry. Note that as a crystal polymorphism of sodium lauryl sulfate, a monohydrate, a ½ hydrate, a ⅛ hydrate and a non-solvate are known (Journal of Crystal Growth 263 (2004) 480-490). Any of the crystals can be used in the composition or formulation of the present invention.

Examples of the excipient which may be contained in the granule (i) of the present invention include starches such as corn starch, potato starch, wheat flour starch, rice starch, partial pregelatinized starch, pregelatinized starch and porous starch; sugar or sugar alcohols such as lactose hydrate, fructose, glucose, mannitol and sorbitol; and anhydrous dibasic calcium phosphate, crystalline cellulose, precipitated calcium carbonate and calcium silicate. Examples of preferable excipient may include starches such as starch, potato starch and corn starch; lactose hydrate, crystalline cellulose and anhydrous dibasic calcium phosphate, and more preferable excipient is lactose hydrate. The amount of excipient which is used in the present invention is preferably 5 to 60 parts by weight, and more preferably, 5 to 45 parts by weight based on 100 parts by weight of the composition or formulation.

Note that if the formulation of the present invention is a formulation having a coating film such as a capsule and a coated tablet, the amount used refers to the amount used based on the total amount of the components to be covered with the coating film (or the total amount of the components to be put in a capsule, or the total amount of the components covered with a coating film).

Examples of the binder which may be contained in the granule (i) of the present invention may include hydroxypropylcellulose, polyvinylpyrrolidone, macrogol and similar compounds as mentioned in the excipient. Specific examples of the binder include hydroxypropylcellulose, hydroxypropylmethylcellulose, methylcellulose, povidone (polyvinylpyrrolidone) and powdered acacia, and preferable binder is hydroxypropylcellulose. The amount of binder used is preferably 0.1 to 50 parts by weight, further preferably 0.5 to 40 parts by weight and further more preferably 0.5 to 10 parts by weight based on 100 parts by weight of the composition or formulation.

Note that if the formulation of the present invention is a formulation having a coating film such as a capsule and a coated tablet, the amount used refers to the amount used based on the total amount of the components to be covered with the coating film (or the total amount of the components to be put in a capsule, or the total amount of the components covered with a coating film).

Examples of preferable lubricants which may be contained in the granule (i) of the present invention include magnesium stearate, calcium stearate, talc, sucrose fatty acid ester and sodium stearyl fumarate.

Examples of the stabilizer which may be contained in the granule (i) of the present invention may include para-oxybenzoates such as methyl paraben and propyl paraben; alcohols such as chlorobutanol, benzyl alcohol and phenylethyl alcohol; benzalkonium chloride, phenols such as phenol and cresol, thimerosal, dehydroacetic acid and sorbic acid.

Examples of the flavoring agent which may be contained in the granule (i) of the present invention may include a sweetener, an acidulant and a fragrance usually used.

The granule (i) of the present invention is produced by granulating a composition comprising the compound represented by formula (I) or a salt thereof, and optionally, additive(s) such as a disintegrating agent, a solubilizing agent, an excipient, a lubricant, a coating agent, a binder, a stabilizer, a flavoring agent and a diluent.

In the present invention, the "pharmaceutical composition" refers to a mixture comprising two or more substances which is used for treating and preventing a disease. According to an aspect of the present invention, the pharmaceutical composition is used for production of a pharmaceutical formulation.

In the present invention, the "pharmaceutical formulation" refers to a formulation for treating and preventing a disease.

In the present invention, the "oral formulation" refers to a formulation that can be orally administered. The oral administration refers to swallowing a formulation so as to enter the gastrointestinal tract and an active ingredient is mainly absorbed through the intestinal tract.

Specific examples of the oral formulation include solid formulations such as a tablet, a capsule, a solution, a powder, a lozenge, a chewable agent, a granule, a gel, a film agent and a spray and liquid formulations. Examples of the liquid formulation include a suspension, a solution, syrup and an elixir. Such a formulation can be used as filler in soft or hard capsules. Generally, as a carrier, for example, water, ethanol, polyethylene glycol, propylene glycol, methylcellulose, or appropriate oil, and one or more emulsifiers and/or a suspending agent are used. A liquid formulation can be also prepared by dissolving a unit-dose solid medicinal agent, for example, dissolving a pharmaceutical composition in a package into a carrier such as water.

In the present invention, "ALK" stands for "Anaplastic Lymphoma Kinase" and refers to a receptor tyrosine kinase belonging to an insulin receptor family.

In the present invention, as a salt of the compound represented by formula (I), a hydrochloride is preferable and a monohydrochloride is more preferable.

The compound represented by formula (I) or a salt thereof can be produced by the method(s) etc. disclosed in Patent Literatures 2 to 4.

In the present invention, the compound represented by formula (I) or a salt thereof include a hydrate, a pharmaceutically acceptable solvate and a crystal polymorphism.

In one aspect of the present invention, a monohydrochloride of the compound represented by formula (I) is a crystal (hereinafter, referred to as Form I crystal) having a powder X-ray diffraction pattern in which peaks are present at diffraction angles (2θ) of 8.4°, 14.0°, 16.7°, 18.8° and 23.3°. Form I crystal can be obtained by adding the compound represented by formula (I) dropwise in a solution mixture of ethanol and hydrochloric acid (containing 1 mole equivalent or more of hydrochloric acid to the compound of formula (I)) while keeping the temperature of the solution mixture at about 35° C. or more.

An example of the measurement results of powder X-ray diffraction of Form I crystal is shown in FIG. 1 and a peak in the powder X-ray diffraction pattern will be shown below.

TABLE 1

| Diffraction angle 2θ | | |
|---|---|---|
| 3.5 | 20.2 | 28.8 |
| 8.0 | 20.5 | 29.5 |
| 8.4 | 21.0 | 29.9 |
| 8.7 | 21.5 | 30.8 |
| 11.0 | 21.8 | 31.3 |
| 11.9 | 22.1 | 31.8 |
| 12.1 | 22.3 | 31.9 |
| 14.0 | 22.6 | 32.6 |
| 15.1 | 22.9 | 33.1 |
| 15.6 | 23.3 | 33.2 |
| 16.1 | 24.1 | 33.8 |
| 16.4 | 24.8 | 34.7 |
| 16.7 | 25.4 | 35.3 |
| 17.1 | 25.7 | 35.5 |
| 17.5 | 26.1 | 36.4 |
| 18.2 | 26.9 | 36.6 |
| 18.8 | 27.7 | 37.5 |
| 19.0 | 27.9 | 38.8 |
| 19.1 | 28.2 | 39.4 |

In the present invention, analysis of powder X-ray diffraction can be made, for example, by a customary method such as the "powder X-ray diffraction measurement method" described in the Japanese pharmacopeia (15th revised). The Japanese pharmacopeia describes that diffraction angles 2θ of the same types of crystals usually match with each other within the range of ±0.2 degrees. Therefore, not only a crystal having a peak diffraction angle in the powder X-ray diffraction completely matches but also a crystal having a peak diffraction angle matched with an error range of about ±0.2 degrees is included in the present invention.

An example of the measurement conditions of powder X-ray diffraction analysis are shown below:
Measurement apparatus: X'Pert-Pro MPD (manufactured by PANalytical)
Anticathode: Cu
Tube voltage: 45 kV
Tube current: 40 mA
Step width: 0.017
Scanning axis: 2θ
Sampling time per step: 43 seconds
Scanning range: 3 to 40°

The pharmaceutical composition or formulation is a composition or formulation having a good solubility which comprises (i) a glanule containing a compound of formula (I) and a salt thereof and (ii) a disintegrating agent.

In the present invention, the "composition or formulation having good solubility" or "formulation improved in solubility" is, for example, a formulation having a drug substance dissolution rate of 65% or more 75 minutes after initiation of the dissolution test at 37° C., preferably, 70% or more at 75 minutes after initiation of the dissolution test at 37° C., more preferably, a dissolution rate of 40% or more at 30 minutes after initiation of a dissolution test at 37° C. and 65% or more at 75 minutes after initiation of a dissolution test at 37° C., and particularly, a dissolution rate of 40% or more at 30 minutes after initiation of a dissolution test at 37° C. and 70% or more at 75 minutes after initiation of a dissolution test at 37° C.

In the above dissolution test, the dissolution test by the paddle method (specified in the Japanese pharmacopeia 16$^{th}$ edition) is performed by using 1st fluid for dissolution test defined in the Japanese Pharmacopenia 16$^{th}$ edition (900 mL) containing polyoxyethylene (10) octyl phenyl ether (4%) at 100 rotations/minute.

The formulation of the present invention can be produced by mixing the granules (i) of the present invention, a disintegrating agent and, optionally, additives, and subjecting the mixture to a general production process, preferably by the following production processes.

1) Mix the compound represented by formula (I) and additives such as a disintegrating agent, a solubilizing agent, an excipient and a binder, and granulate the mixture while adding or spraying a solvent (for example, purified water, ethanol or solution mixture thereof). Add to the granulated substance (granule) thus obtained a disintegrating agent (ii) and optionally an appropriate amount of additives such as lubricant or fluidizers, and mix them and charge capsules with the resultant mixture or subject the resultant mixture to compression molding.

2) Mix the compound represented by formula (I) and additives such as a disintegrating agent, a solubilizing agent and an excipient, and granulate the mixture while adding or spraying a liquid obtained by dispersing or dissolving a binder and, if necessary, other additives in a solvent (for example, purified water, ethanol or a solution mixture thereof). Add to the granulated substance obtained (granule) a disintegrating agent (ii) and optionally an appropriate amount of additives such as lubricant or fluidizers, and mix them and charge capsules with the resultant mixture or subject the resultant mixture to compression molding, for example.

In the methods 1) and 2), a granule obtained by means of e.g., dry granulation or heat granulation in place of wet granulation may be used.

The composition and formulation of the present invention may contain a lubricant or a fluidizer in addition to the disintegrating agent (ii) as an external additive. Examples of the lubricant and fluidizer may include magnesium stearate, calcium stearate, talc, sucrose fatty acid ester and sodium stearyl fumarate. Preferably, magnesium stearate may be mentioned. The use amount of lubricant and fluidizer is preferably 0.01 to 20 parts by mass based on the composition or formulation (100 parts by weight) and further preferably 0.05 to 15 parts by weight. Note that, if the formulation of the present invention is a formulation having a coating film such as a capsule and a coated tablet, the use amount refers to that based on the total amount of the components to be covered with the coating film (the total amount of the components to be put in a capsule, or the total amount of the components covered with a coating film).

An appropriate coating agent can be further applied to tablets to obtain sugar coated tablets or film coated tablets.

As the base for a sugar-coating material, for example, a sugar or a sugar alcohol such as sucrose and erythritol is used, and one or more substances selected from talc, precipitated calcium carbonate, gelatin, gum arabic, pullulan, carnauba wax, etc. may be used in combination with the sugar or the sugar alcohol.

Examples of the coating material may include ethylcellulose, hydroxypropylcellulose, hydroxypropylmethylcellulose, shellac, talc, carnauba wax and paraffin.

Examples of a base for an enteric film coating material include cellulose polymers such as hydroxypropylmethylcellulose phthalate, hydroxypropylmethylcellulose acetatesuccinate, carboxymethylethylcellulose and cellulose acetate phthalate; acrylic acid polymers such as methacrylic acid copolymer L [EUDRAGIT L (trade name), Evonik Degussa], methacrylic acid copolymer LD [EUDRAGIT L-30D55 (trade name), Evonik Degussa] and methacrylic acid copolymer S [EUDRAGIT S (trade name), Evonik Degussa]; and natural products such as shellac.

Examples of a base for a sustained-release film coating material include cellulose polymers such as ethylcellulose; acrylic acid polymers such as aminoalkyl methacrylate copolymer RS [EUDRAGIT RS (trade name), Evonik Degussa], an ethyl acrylate-methyl methacrylate copolymer suspension solution [EUDRAGIT NE (trade name), Evonik Degussa]; and cellulose acetate.

Two types or more of the bases for coating materials mentioned above may be mixed in an appropriate ratio and put in use.

To the coating material, if necessary, e.g., a water-soluble substance for controlling a dissolution rate and a plasticizer may be added. As the water-soluble substance, one or more substance selected from a water-soluble polymer such as hydroxypropylmethylcellulose; a sugar alcohol such as mannitol; a sugar such as sucrose and anhydrous maltose; a surfactant such as sucrose fatty acid ester and polyoxyethylene polyoxypropylene glycol, polysorbate and sodium lauryl sulfate, etc. can be used. As the plasticizer, one or more substance selected from acetylated monoglyceride, triethyl citrate, triacetin, dibutyl sebacate, dimethyl sebacate, middle-chain fatty acid triglyceride, acetyltriethyl citrate, tributyl citrate, acetyltributyl citrate, dibutyl adipate, oleic acid, oleynol, etc. can be used.

As a method for coating tablets with the coating material, a general method can be used. Examples thereof include a pan coating method, a fluid coating method, a roll coating method and a fluid/roll coating method. The coating liquid to be used in such a method is obtained by mixing the base for a coating material, talc and a solvent (preferably, ethanol or a mixture of ethanol and water). The concentration of a solid content of such a coating liquid preferably falls within the range of 5 to 15 mass % based on the total mass of such a coating liquid.

The compound represented by formula (I) or a salt thereof has an excellent ALK inhibitory action and excellent stability in a living body and is useful as a preventive or therapeutic agent (particularly therapeutic agent) for proliferative diseases. More specifically, the compound represented by formula (I) or a salt thereof is useful as a preventive or therapeutic agent (particularly therapeutic agent) for diseases such as various types of cancers like leukemia (e.g., acute myelogenous leukemia, chronic myelogenous leukemia, acute lymphocytic leukemia, chronic lymphocytic leukemia), malignant lymphoma (e.g., Hodgkin's lymphoma, non-Hodgkin's lymphoma), brain tumor, neuroblastoma, glioma, thyroid cancer, myelodysplastic syndrome, head and neck cancer, esophageal cancer, stomach cancer, colon cancer, colorectal cancer, breast cancer, ovarian cancer, lung cancer, pancreatic cancer, liver cancer, gallbladder cancer, skin cancer, malignant melanoma, kidney cancer, renal pelvis ureter cancer, bladder cancer, ovarian cancer, uterine cancer, testicular cancer and prostate cancer. The compound or a salt thereof of the present invention is also useful as a preventive or therapeutic agent (particularly therapeutic agent) for infiltration and metastasis of a solid cancer. The compound or a salt thereof of the present invention is also effective as a preventive or therapeutic agent for other diseases in connection with ALK such as depression or cognitive dysfunction.

When the composition of the present invention is used as an ALK inhibitor or a therapeutic or preventive agent for a proliferative disease or depression or a therapeutic or preventive agent for cognitive dysfunction, the composition is administered orally, rectally, parenterally (intravenously, intramuscularly, subcutaneously), intracisternally, intravaginally, intraperitoneally, intravesically and locally (intravenous drip, powder, ointment, gel or cream) and through inhalation (oral or nose spray). Examples of the dosage form thereof include tablet, capsule, granule, powder, pill, aqueous and nonaqueous oral solution and suspension, and parenteral solution put in small containers for a unit dose. The dosage form may be designed so as to adapt to various methods for administrating a formulation including a controlled release formulation to be subcutaneously grafted.

The dosage form is preferably oral administration by tablets, capsules, granules or powder formulation.

When the composition of the present invention is used as an ALK inhibitor or a therapeutic or preventive agent for a proliferative disease or depression or cognitive dysfunction, the dosage of the active ingredient (a compound represented by formula (I) or a salt thereof of the present invention) may vary depending upon the symptom, age, body weight, relative health condition, other medication, administering method, etc. For example, a generally effective amount of active ingredient (the compound or a salt thereof of the present invention represented by formula (I)) to a patient (a warm-blooded animal, particularly a human) orally administered is preferably 0.001 to 1000 mg and further preferably 0.01 to 300 mg per body weight (1 kg) per day. The dosage thereof used per day preferably falls within the range of 1 to 1500 mg per adult patient having an ordinary body weight. In the case of a parenteral agent, the amount thereof used is preferably 0.001 to 1000 mg and further preferably 0.01 to 300 mg per body weight (1 kg) per day. It is desirable that the amount thereof used is administered once per day or administered depending upon the symptom by dividing the amount used into several portions.

The composition of the present invention preferably contains the compound represented by formula (I) or a salt thereof in an amount of, for example, 20 to 70 wt %, preferably, 30 to 60 wt %, and especially preferably, 35 to 60 wt % in terms of the free form based on the total amount of the composition.

The formulation of the present invention preferably contains the compound represented by formula (I) or a salt thereof in an amount of, for example, 20 to 70 wt %, preferably, 30 to 60 wt %, and especially preferably, 35 to 60 wt % in terms of the free form based on the total amount of the formulation. Note that, if the formulation of the present invention is a formulation having a coating film such as a capsule and a coated tablet, the content refers to the content based on the total amount of the components to be covered with the coating film (or the total amount of the components to be put in a capsule, or the total amount of the components covered with a coating film). More specifically, if the formulation of the present invention is a capsule, the compound represented by formula (I) or a salt thereof is preferably contained in an amount of, for example, 20 to 70 wt %, preferably, 30 to 60 wt %, and especially preferably, 35 to 60 wt % in terms of the free form based on the total amount of the components to be put in a capsule.

The formulation of the present invention preferably contains the compound represented by formula (I) or a salt thereof in an amount of, for example, 60 to 240 mg, preferably, 100 to 200 mg, and especially preferably, 140 mg to 190 mg in terms of the free form per unit formulation.

According to another aspect of the present invention, the following inventions (4-1) to (4-7) are provided.

(4-1)

A pharmaceutical formulation comprising a compound less soluble or insoluble in water and sodium lauryl sulfate, in which the sodium lauryl sulfate is obtained by crystallization.

(4-2)
The formulation according to (4-1), wherein the sodium lauryl sulfate is a crystal of a ⅛ hydrate.

(4-3)
A method for producing a pharmaceutical formulation improved in solubility of a compound less soluble or insoluble in water, comprising blending sodium lauryl sulfate crystallized and optionally other additives with the compound.

(4-4)
A method for manufacturing a pharmaceutical formulation having an improved solubility of a compound which is less soluble or insoluble in water, characterized in that the method comprises blending NIKKOL SLS as sodium lauryl sulfate and optionally other additive(s) with the compound.

(4-5)
A method for improving solubility of a compound less soluble or insoluble in water contained in a pharmaceutical formulation, comprising blending sodium lauryl sulfate obtained by crystallization and optionally other additives with the compound.

(4-6)
A method for improving solubility of a compound which is less soluble or insoluble in water contained in a pharmaceutical formulation, characterized in that the method comprises blending NIKKOL SLS as sodium lauryl sulfate and optionally other additive(s) with the compound.

(4-7)
The method according to any of (4-3) to (4-6), wherein the sodium lauryl sulfate is a crystal of a ⅛ hydrate.

In the inventions of (4-1) to (4-7), the "less soluble or insoluble in water" means that solubility of a compound to water at 25° C. is less than 100 μg/mL. According to an aspect of the present invention, the solubility of the "compound less soluble or insoluble in water" at 25° C. is less than 10 μg/mL. The solubility can be measured in accordance with a conventional method. As an example of the compound less soluble or insoluble in water, 9-ethyl-6,6-dimethyl-8-(4-morpholin)-4-yl-piperidin-1-yl)-11-oxo-6,11-dihydro-5H-benzo[b]carbazole-3-carbonitrile and a salt thereof may be mentioned.

In the inventions of (4-1) to (4-7), "crystallization" means that a crystal of sodium lauryl sulfate is precipitated from a solution or suspension containing sodium lauryl sulfate.

In the inventions of (4-1) to (4-7), the term "solubility is improved" and "a pharmaceutical formulation improved in solubility" mean, for example, drug substance dissolution rate is 65% or more 75 minutes after initiation of a dissolution test at 37° C., preferably, 70% or more 75 minutes after initiation of a dissolution test at 37° C., and a formulation which has the above dissolution profile, respectively. In the above dissolution test, a dissolution test by the paddle method (specified in the Japanese pharmacopeia 16$^{th}$ edition) is performed by using 1st fluid for dissolution test defined in the Japanese Pharmacopenia 16$^{th}$ edition (900 mL) containing polyoxyethylene (10) octyl phenyl ether (4%) at 100 rotations/minute.

The meaning of the term of "pharmaceutical formulation" in (4-1) to (4-7) is the same as defined above.

The formulations according to (4-1) to (4-7) are produced by a method well known in the art using a compound less soluble or insoluble in water, sodium lauryl sulfate, and optional additives such as an excipient, a disintegrating agent, a binder, a lubricant, a coating agent, a stabilizer, a flavoring agent and a diluent, or can be produced based on the method described in the specification of the present application.

Examples of the excipient may include starches such as corn starch, potato starch, wheat flour starch, rice starch, partial pregelatinized starch, pregelatinized starch and porous starch; sugar or sugar alcohols such as lactose hydrate, fructose, glucose, mannitol and sorbitol; and anhydrous dibasic calcium phosphate, crystalline cellulose, precipitated calcium carbonate and calcium silicate. As the disintegrating agent, for example, the same compounds as those mentioned as the excipient and croscarmellose sodium and chemically modified starches and celluloses such as sodium starch glycolate, cross-linked polyvinylpyrrolidone may be mentioned. Specific examples of the disintegrating agent that is to be used may include sodium starch glycolate, carboxymethylcellulose, carboxy methylcellulose calcium, carboxymethyl starch sodium, croscarmellose sodium, crospovidone, low-substituted hydroxypropylcellulose, hydroxypropyl starch, etc. As the binder, for example, polyvinylpyrrolidone, macrogol and the same compounds as mentioned in the excipient may be mentioned. Specific examples of the binder may include hydroxypropylcellulose, hydroxypropylmethylcellulose, methylcellulose, povidone (polyvinylpyrrolidone) and powdered acacia. As the lubricant, for example, magnesium stearate, calcium stearate, talc, sucrose fatty acid ester and sodium stearyl fumarate may be mentioned.

As a crystal polymorphism of sodium lauryl sulfate, a monohydrate, a ½ hydrate, a ⅛ hydrate and a non-solvate are known (Journal of Crystal Growth 263 (2004) 480-490). Any of the crystal can be used in the inventions of (4-1) to (4-7).

EXAMPLES

Now, the present invention will be more specifically described by way of Examples; however, the present invention is not limited by these. Note that, in Examples 1 to 27, as sodium lauryl sulfate, NIKKOL SLS ((product name, Nikko Chemicals Co., Ltd.) was used.

Examples 1 to 7: Relationship Between SLS Addition, SLS Amount and Solubility of Drug Substance (1) Production of Formulation In accordance with the amounts of components shown in Table 2, six formulations different in amount of sodium lauryl sulfate (SLS) were prepared. Individual components for each granular formulation were fed in a high-shear granulator and preparatorily mixed. An appropriate amount of purified water was sprayed to the mixture and the mixture was mixed, granulated and vacuum dried to obtain dried powder. The dried powder was adjusted by a sizer. The obtained granules and external components (carmellose calcium, magnesium stearate) were mixed by a mixer to obtain a powder blend. Capsule containers were each charged with the powder blend to produce an encapsulated formulation.

TABLE 2

Examples 1-7 (amount per capsule, mg)

| | Name | Example 1 | Example 2 | Example 3 | Example 4 | Example 5 | Example 6 | Example 7 |
|---|---|---|---|---|---|---|---|---|
| | Rate of compound (free) of formula (I) to SLS | 100:50 | 100:37.5 | 100:25 | 100:12.5 | 100:6 | 100:3 | 100:0 |
| Component of granule | Hydrochloride of compound of formula (I) | 161.33 | 161.33 | 161.33 | 161.33 | 161.33 | 161.33 | 161.33 |
| | Lactose hydrate | 33.67 | 52.42 | 71.17 | 89.92 | 99.67 | 104.17 | 108.67 |
| | Hydroxypropylcellulose | 15.00 | 15.00 | 15.00 | 15.00 | 15.00 | 15.00 | 15.00 |
| | Sodium lauryl sulfate | 75.00 | 56.25 | 37.50 | 18.75 | 9.00 | 4.50 | 0.00 |
| | Carmellose calcium | 15.00 | 15.00 | 15.00 | 15.00 | 15.00 | 15.00 | 15.00 |
| External component | Carmellose calcium | 28.35 | 28.35 | 28.35 | 28.35 | 28.35 | 28.35 | 28.35 |
| | Magnesium stearate | 1.65 | 1.65 | 1.65 | 1.65 | 1.65 | 1.65 | 1.65 |
| | Total | 330.00 | 330.00 | 330.00 | 330.00 | 330.00 | 330.00 | 330.00 |

(2) Evaluation of Formulation and the Results

Formulations of Examples 1 to 4 and 7 were subjected to the dissolution test by the paddle method (specified in the Japanese pharmacopeia) performed by using 1st fluid (900 mL) containing polyoxyethylene (10) octyl phenyl ether (5%) specified in the dissolution test according to the Japanese pharmacopeia, at 37° C. and 100 rotations/minute. The dissolution profile is shown in FIG. 2. Formulations of Examples 1 and 4 to 7 were subjected to the dissolution test by the paddle method (specified in the Japanese pharmacopeia) performed by using 1st fluid (900 mL) containing polyoxyethylene (10) octyl phenyl ether (4%) specified by the dissolution test according to the Japanese pharmacopeia, at 37° C. and 100 rotations/minute. The dissolution profile is shown in FIG. 3.

(3) Conclusion

As is shown in dissolution profiles of FIG. 2 and FIG. 3, the formulations of Examples 1 to 6 containing SLS were all improved in dissolution compared to the formulation of Example 7 containing no SLS. More specifically, it was demonstrated that as the amount of SLS in a formulation increases, solubility tends to be improved and that solubility is significantly improved if SLS is contained in a pharmaceutical formulation even slightly, as is apparent particularly from comparison between Examples 6 and 7 in FIG. 3.

Examples 8 and 9: Relationship Between Particle Diameter of Granule and Solubility of Drug Substance (1) Production of Formulation In accordance with the amounts of components shown in Table 3, two formulations different in granular particle diameter were prepared by adjusting the amount of purified water. Individual components for each granular formulation were fed in a high-shear granulator and preparatorily mixed. The purified water shown in Table 2 was sprayed to the mixture and the mixture was mixed, granulated and vacuum dried to obtain dried powder. The dried powder was adjusted by a sizer. The obtained size-regulated granules and external components (carmellose calcium, magnesium stearate) were mixed by a mixer to obtain a powder blend. Capsule containers were each charged with the powder blend to produce an encapsulated formulation.

TABLE 3

Examples 8 and 9 (amount per capsule, mg)

| | Name | Example 8 | Example 9 |
|---|---|---|---|
| | Amount of purified water (ratio relative to weight of components of granule, %)) | 15 | 17 |
| Component of granule | Hydrochloride of compound of formula (I) | 161.33 | 161.33 |
| | Lactose hydrate | 33.67 | 33.67 |
| | Hydroxypropylcellulose | 15.00 | 15.00 |
| | Sodium lauryl sulfate | 75.00 | 75.00 |
| | Carmellose calcium | 15.00 | 15.00 |
| External component | Carmellose calcium | 28.35 | 28.35 |
| | Magnesium stearate | 1.65 | 1.65 |
| | Total | 330.00 | 330.00 |

(2) Evaluation of Formulation and the Results

Particle size distribution of size-regulated granules was measured. The mean particle diameter was 172 μm in Example 8 and 300 μm in Example 9. Formulations of Examples 8 and 9 were subjected to the dissolution test by the paddle method (specified in the Japanese pharmacopeia) performed by using 1st fluid (900 mL) containing polyoxyethylene (10) octyl phenyl ether (5%) specified by the dissolution test according to the Japanese pharmacopeia, at 37° C. and 100 rotations/minute. The dissolution profiles are shown in FIG. 4.

Note that the mean particle diameter was obtained by feeding a 6 g of granulated substance sampled onto the top of the stacked sieves different in mesh size (mesh size: 850, 500, 355, 250, 180, 106, 75, 53, 0 μm), shaking the sieves for 3 minutes, measuring the weights of granulated substances remaining on the individual sieves, and calculating the particle diameter of the granules which have a cumulative percentage of 50% by means of approximation of logarithmic normal distribution from the mesh size of the sieve and cumulative weight percentage undersize.

(3) Conclusion

As shown in FIG. 3, it was demonstrated that the formulation of Example 9 having a larger granule particle diameter is improved in solubility.

It is reported that if the particle diameter of a granule is large, solubility decreases (Ikumasa Ohno, "Pharmaceutical study on production parameter influencing on solubility of pharmaceutical product in granulating step", http://miti-zane.ll.chiba-u.jp/metadb/up/irwg10/IY-K-Y-049.pdf, International Journal of Pharmaceutics 338 (2007) 79-86). It was totally beyond expectation that a formulation having a larger granule in diameter is improved in solubility.

Examples 10 to 14: Relationship Between Addition Method and Amount of Disintegrating Agent and Solubility of Drug Substance (1) Production of Formulation In accordance with the amounts of components shown in Table 4, five formulations different in amount of carmellose calcium to be added as an external component were prepared. Individual components for each granular formulation were fed in a high-shear granulator and preparatorily mixed. An appropriate amount of purified water was sprayed to the mixture and the mixture was mixed, granulated and vacuum dried to obtain dried powder. The dried powder was adjusted by a sizer. The obtained granules and the external component (carmellose calcium) were mixed to obtain a powder blend. Capsule containers were each charged with the powder blend to produce an encapsulated formulation.

TABLE 4

Examples 10 to 14 (amount per capsule, mg)

| Name | | Example 10 | Example 11 | Example 12 | Example 13 | Example 14 |
|---|---|---|---|---|---|---|
| Ratio (wt %) of carmellose calcium added as external additive to powder blend | | 0 | 3 | 5 | 10 | 25 |
| Component of granule | Hydrochloride of compound of formula (I) | 161.33 | 161.33 | 161.33 | 161.33 | 161.33 |
| | Hydroxypropylcellulose | 13.15 | 13.15 | 13.15 | 13.15 | 13.15 |
| | Sodium lauryl sulfate | 80.67 | 80.67 | 80.67 | 80.67 | 80.67 |
| | Sodium starch glycolate | 7.89 | 7.89 | 7.89 | 7.89 | 7.89 |
| External component | Carmellose calcium | 0.00 | 8.14 | 13.84 | 29.23 | 87.68 |

(2) Evaluation of Formulation and the Results

Formulations of Examples 10 to 14 were subjected to the dissolution test by the paddle method (specified in the Japanese pharmacopeia) performed by using 1st fluid (900 mL) containing polyoxyethylene (10) octyl phenyl ether (7%) specified by the dissolution test according to the Japanese pharmacopeia, at 37° C. and 100 rotations/minute. The dissolution profiles are shown in FIG. 5.

(3) Conclusion

As shown in FIG. 5, the formulations containing the external additive (3 to 5 wt %) were slightly improved in dissolution compared to the formulation containing no external additive. Solubility was significantly improved by adding 10 wt % or more of the external additive.

Examples 15 to 25: Relationship Between Predetermined Disintegrating Agents Including Carmellose Calcium and Solubility of Drug Substance (1) Production of Formulation To the granules prepared in Example 10, external components (11 types in total, Examples 15 to 25) shown in Table 5 were separately added and mixed to obtain powder blends. The blending ratio of the granules prepared in Example 10 was 9 parts by weight and the blending ratio of the external additive was 1 part by weight. Capsule containers were each charged with the powder blend to produce an encapsulated formulation.

TABLE 5

Type of external component (Examples 15 to 25)

| Example 15 | Sodium starch glycolate |
| Example 16 | Low-substituted hydroxypropylcellulose |
| Example 17 | Carmellose calcium |
| Example 18 | Sodium hydrogen carbonate |
| Example 19 | Pregelatinized starch |
| Example 20 | Sodium chloride |
| Example 21 | Corn starch |
| Example 22 | Croscarmellose sodium |
| Example 23 | Crystalline cellulose |
| Example 24 | Silicic anhydride |
| Example 25 | Carmellose |

(2) Evaluation of Formulation and the Results

Formulations of Examples 10 and 15 to 25 were subjected to the dissolution test by the paddle method (specified in the Japanese pharmacopeia) performed by using 1st fluid (900 mL) containing polyoxyethylene (10) octyl phenyl ether (7%) specified by the dissolution test according to the Japanese pharmacopeia, at 37° C. and 100 rotations/minute. The dissolution profiles are shown in FIG. 6-1 and FIG. 6-2.

(3) Conclusion

As shown in FIG. 6, it was demonstrated that the disintegrating agents showing high solubility are low-substituted hydroxypropylcellulose (Example 16), carmellose calcium (Example 17), sodium hydrogen carbonate (Example 18) and pregelatinized starch (Example 19).

A volume of low-substituted hydroxypropylcellulose and carmellose calcium became 5 times or more and that of croscarmellose sodium, sodium starch glycolate and pregelatinized starch became 2.5 times or more when adding 20 ml of 1st fluid for dissolution test defined in the Japanese Pharmacopenia 16$^{th}$ edition to per 1.0 g of the disintegrating agent.

Examples 26 and 27: Comparison of Disintegrating Agents (1) Production of Formulation In accordance with the amounts of components shown in Table 6, two formulations were prepared by varying the formulation of the disintegrating agent using low-substituted hydroxypropylcellulose and carmellose calcium as a disintegrating agent. Individual components for each granular formulation were fed in a high-shear granulator and preparatorily mixed. An appropriate amount of purified water was sprayed to the mixture and the mixture was mixed, granulated and vacuum dried to obtain dried powder. The dried powder was adjusted by a sizer. The obtained granules and an external component were mixed by a mixer to obtain a powder blend. Capsule containers were each charged with the powder blend to produce an encapsulated formulation. Note that the components of the formulation of Example 26 are the same as in Example 1.

TABLE 6

Examples 26 and 27 (amount per capsule, mg)

|  | Name | Example 26 | Example 27 |
|---|---|---|---|
| Component of granule | Hydrochloride of compound of formula (I) | 161.33 | 161.33 |
|  | Lactose hydrate | 33.67 | 52.42 |
|  | Hydroxypropylcellulose | 15.00 | 15.00 |
|  | Sodium lauryl sulfate | 75.00 | 56.25 |
|  | Carmellose calcium | 15.00 | 0.00 |
|  | Low-substituted hydroxypropylcellulose | 0.00 | 15.00 |
| External component | Carmellose calcium | 28.35 | 0.00 |
|  | Low-substituted hydroxypropylcellulose | 0.00 | 28.35 |
|  | Magnesium stearate | 1.65 | 1.65 |
|  | Total | 330.00 | 330.00 |

(2) Evaluation of Formulation and the Results

Formulations of Examples 26 and 27 were subjected to the dissolution test by the paddle method (specified in the Japanese pharmacopeia) performed by using 1st fluid (900 mL) containing polyoxyethylene (10) octyl phenyl ether (5%) specified by the dissolution test according to the Japanese pharmacopeia, at 37° C. and 100 rotations/minute. The dissolution profiles are shown in FIG. 7.

As shown in FIG. 7, formulations separately using low-substituted hydroxypropylcellulose and carmellose calcium as a disintegrating agent both showed satisfactory solubility. In consideration of individual variations of data, it was demonstrated that the formulation using carmellose calcium is rather better.

Examples 28 and 29: Comparison of Sodium Lauryl Sulfate Products (1) Production of Formulation Using different products of sodium lauryl sulfate, two formulations were prepared in accordance with the amount of components shown in Table 7. Individual components for each granular formulation were fed in a high-shear granulator and preparatorily mixed. An appropriate amount of purified water was sprayed to the mixture and the mixture was mixed, granulated and vacuum dried to obtain dried powder. The dried powder was adjusted by a sizer. The obtained size-regulated granules and external components were mixed by a mixer to obtain a powder blend. Capsule containers were each charged with the powder blend to produce an encapsulated formulation. Note that crystals of sodium lauryl sulfate used in these Examples were analyzed by powder X-ray diffraction. It was confirmed that the crystals are ⅛ hydrates.

TABLE 7

Examples28 and 29 (amount per capsule, mg)

|  | Name | Example 28 | Example 29 |
|---|---|---|---|
| Component of granule | Hydrochoride of compound of formula (I) | 161.33 | 161.33 |

TABLE 7-continued

Examples28 and 29 (amount per capsule, mg)

|  | Name | Example 28 | Example 29 |
|---|---|---|---|
|  | Lactose hydrate | 33.67 | 33.67 |
|  | Hydroxypropylcellulose | 15.00 | 15.00 |
|  | Sodium lauryl sulfate (NIKKOL SLS) | 75.00 | 0.00 |
|  | Sodium lauryl sulfate (Kolliphor ® SLS Fine) | 0.00 | 75.00 |
|  | Carmellose calcium | 15.00 | 15.00 |
| External component | Carmellose calcium | 28.35 | 28.35 |
|  | Magnesium stearate | 1.65 | 1.65 |
|  | Total | 330.00 | 330.00 |

(2) Evaluation of Formulation and the Results

Examples 28 and 29 were subjected to the dissolution test by the paddle method (specified in the Japanese pharmacopeia) performed by using 1st fluid (900 mL) containing polyoxyethylene (10) octyl phenyl ether (4%) specified in the dissolution test according to the Japanese pharmacopeia as a test solution at 37° C. and 100 rotations/minute. The dissolution profile is shown in FIG. 8.

As is shown in FIG. 8, it was found that a formulation using NIKKOL SLS (NIKKO Chemicals) has higher solubility than that using Kolliphor® SLS Fine (BASF), beyond expectation.

As a result of observation of the properties of each products of Sodium lauryl sulfate which were used in the examples, it was considered that NIKKOL SLS (Nikko Chemicals) is obtained through crystallization and Kolliphor® SLS Fine (BASF) is obtained through spray drying. These results suggest that the manufacturing method of Sodium lauryl sulfate affects the dissolution rate of the formulation.

Example 30: Measurement of Bulk Density and Tapping Density of Granules

Bulk density and tapping density of granules contained in the formulations obtained in Example 1 to 9, 26 and 27 were measured by the Method 2 described in Japanese pharmacopenia 16$^{th}$ edition. The results are shown in table 8.

TABLE 8

| Example no: | Bulk density (g/ml) | Tapping density (g/ml) |
|---|---|---|
| 1 | 0.61 | 0.74 |
| 2 | 0.62 | 0.73 |
| 3 | 0.61 | 0.73 |
| 4 | 0.59 | 0.72 |
| 5 | 0.6 | 0.73 |
| 6 | 0.56 | 0.7 |
| 7 | 0.57 | 0.74 |
| 8 | 0.56 | 0.73 |
| 9 | 0.57 | 0.68 |
| 26 | 0.56 | 0.68 |
| 27 | 0.55 | 0.66 |

Reference Example 1: Form I Crystal of 9-ethyl-6,6-dimethyl-8-(4-morpholin-4-yl-piperidin-1-yl)-11-oxo-6,11-dihydro-5H-benzo[b]carbazole-3-carbonitrile Monohydrochloride 9-Ethyl-6,6-dimethyl-8-(4-morpholin-4-yl-piperidin-1-yl)-11-oxo-6,11-dihydro-5H-benzo[b]carbazole-3-carbonitrile (400 g) was dissolved in a solvent mixture of methyl ethyl ketone (4.8 L), acetic acid (1.44 L) and distilled water (1.68 L) at room temperature. This solution was added dropwise in a mixture of ethanol (12 L) and 2N hydrochloric acid (0.8 L) at 60° C. The precipitated solid substance was obtained by filtration, washed with ethanol (2 L) and dried to obtain Form I crystal (357 g) of monohydrochloride of the title compound.

Reference Example 2: Powder X-Ray Diffraction Analysis

Form I crystal of 9-ethyl-6,6-dimethyl-8-(4-morpholin-4-yl-piperidin-1-yl)-11-oxo-6,11-dihydro-5H-benzo[b]carbazole-3-carbonitrile monohydrochloride was subjected to powder X-ray diffraction in the following conditions. The measurement results of Form I crystal are shown in FIG. 1.
Measurement apparatus: X'Pert-Pro MPD (manufactured by PANalytical)
Anticathode: Cu
Tube voltage: 45 kV
Tube current: 40 mA
Step width: 0.017
Scanning axis: 2θ
Sampling time per step: 43 seconds
Scanning range: 3 to 40°

The invention claimed is:

1. A pharmaceutical formulation comprising (i) a granule containing a compound represented by formula (I)

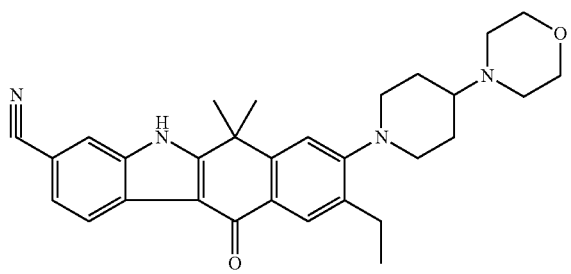

(I)

or a salt thereof and (ii) carmellose calcium as a disintegrating agent, wherein the compound represented by formula (I) or a salt thereof is contained in an amount of 140 mg to 190 mg in terms of the free form per unit formulation.

2. The formulation according to claim 1, wherein the carmellose calcium (ii) is contained in an amount of 5 wt % or more based on the total amount of the formulation.

3. The formulation according to claim 1, wherein the carmellose calcium (ii) is contained in an amount of 7.5 wt % or more based on the total amount of the formulation.

4. The formulation according to claim 1, wherein the granule contains carmellose calcium therein.

5. The formulation according to claim 1, wherein the granule contains a solubilizing agent therein.

6. The formulation according to claim 5, wherein the solubilizing agent is sodium lauryl sulfate.

7. The formulation according to claim 6, wherein sodium lauryl sulfate is obtained by crystallization.

8. The formulation according to claim 5, wherein the weight ratio of the compound represented by formula (I) to the solubilizing agent is 100:2 to 100:60.

9. The formulation according to claim 8, wherein the compound represented by formula (I) or a salt thereof is contained in an amount of 35 to 60 wt % based on the total amount of the formulation.

10. The formulation according to claim 1, wherein the granule contains a binder therein.

11. The formulation according to claim 10, wherein the binder is hydroxypropylcellulose.

12. The formulation according to claim 1, wherein the granule has a mean particle diameter of 150 μm or more.

13. The formulation according to claim 1, wherein the granule has a mean particle diameter of 200 μm or more.

14. The formulation according to claim 1, wherein a compound represented by formula (I) or a salt thereof is contained in an amount of 20 to 70 wt % in terms of the free form based on the total amount of the formulation.

15. A method for producing a formulation improved in solubility of a compound represented by formula (I)

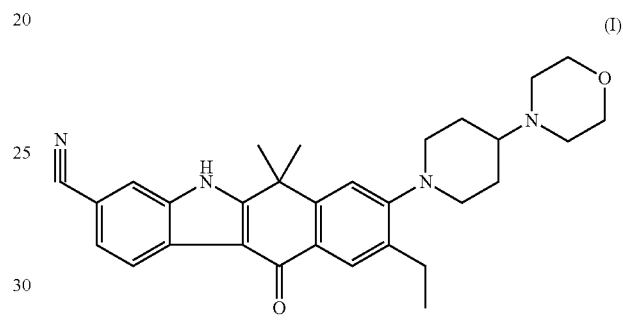

(I)

or a salt thereof, comprising (i) granulating a granule containing a compound represented by formula (I) or a salt thereof and (ii) blending carmellose calcium as a disintegrating agent and optionally other additives as external additives, wherein the compound represented by formula (I) or a salt thereof is contained in an amount of 140 mg to 190 mg in terms of the free form per unit formulation.

16. The method according to claim 15, wherein the carmellose calcium (ii) is contained in an amount of 7.5 wt % or more and 30 wt % or less based on the total amount of the formulation.

17. The method according to claim 15, wherein the granule has a mean particle diameter of 150 μm or more and 1 mm or less.

18. The method according to claim 15, wherein the granule has a mean particle diameter of 180 μm or more and 1 mm or less.

19. The method according to claim 15, wherein the granule (i) has carmellose calcium therein.

20. The method according to claim 15, wherein the granule contains a solubilizing agent therein.

21. The method according to claim 20, wherein the solubilizing agent is sodium lauryl sulfate obtained by crystallization.

22. The method according to claim 20, wherein a weight ratio of the compound represented by formula (I) to the solubilizing agent is 100:2 to 100:60.

23. The method according to claim 15, wherein the granule contains a binder therein.

24. The method according to claim 23, wherein the binder is hydroxypropylcellulose.

* * * * *